(12) United States Patent
Jeong et al.

(10) Patent No.: US 8,559,014 B2
(45) Date of Patent: Oct. 15, 2013

(54) HIGH-RESOLUTION, COMMON-PATH INTERFEROMETRIC IMAGING SYSTEMS AND METHODS

(76) Inventors: Hwan J. Jeong, Los Altos, CA (US); David A. Markle, Saratoga, CA (US)

( * ) Notice: Subject to any disclaimer, the term of this patent is extended or adjusted under 35 U.S.C. 154(b) by 391 days.

(21) Appl. No.: 12/924,244

(22) Filed: Sep. 23, 2010

(65) Prior Publication Data
US 2011/0075928 A1 Mar. 31, 2011

Related U.S. Application Data

(60) Provisional application No. 61/277,506, filed on Sep. 25, 2009, provisional application No. 61/339,324, filed on Mar. 3, 2010.

(51) Int. Cl.
*G01B 9/02* (2006.01)

(52) U.S. Cl.
USPC .......................................................... 356/491

(58) Field of Classification Search
USPC ................ 356/450, 491, 492, 495, 496, 521; 359/370, 371
See application file for complete search history.

(56) References Cited

U.S. PATENT DOCUMENTS

| | | | |
|---|---|---|---|
| 6,259,055 B1 | 7/2001 | Sokol et al. | |
| 6,501,551 B1 | 12/2002 | Tearney et al. | |
| 6,934,035 B2 | 8/2005 | Yang et al. | |
| 7,006,234 B1 * | 2/2006 | Cottrell et al. | 356/515 |
| 7,061,625 B1 | 6/2006 | Hwang et al. | |
| 7,095,507 B1 | 8/2006 | Hwang et al. | |
| 7,138,629 B2 | 11/2006 | Noji et al. | |
| 7,209,239 B2 | 4/2007 | Hwang et al. | |
| 7,259,869 B2 | 8/2007 | Hwang et al. | |
| 7,351,969 B2 | 4/2008 | Watanabe et al. | |
| 7,357,513 B2 | 4/2008 | Watson et al. | |
| 7,365,858 B2 | 4/2008 | Fang-Yen et al. | |
| 7,428,057 B2 | 9/2008 | De Lega et al. | |
| 7,446,882 B2 | 11/2008 | De Lega et al. | |
| 7,616,323 B2 | 11/2009 | De Lega et al. | |
| 7,864,334 B2 * | 1/2011 | Jeong | 356/496 |
| 7,978,403 B2 * | 7/2011 | Brueck et al. | 359/370 |
| 7,986,412 B2 * | 7/2011 | Jeong | 356/450 |
| 2002/0066318 A1 | 6/2002 | Dubois et al. | |
| 2005/0105097 A1 | 5/2005 | Fang-Yen et al. | |
| 2006/0132804 A1 | 6/2006 | Dubois et al. | |
| 2006/0158657 A1 | 7/2006 | De Lega et al. | |
| 2006/0158658 A1 | 7/2006 | De Lega et al. | |

(Continued)

OTHER PUBLICATIONS

Gustafsson et al., "I$^5$M: 3D widefield light microscopy with better than 100 nm axial resolution," Journal of Microscopy, Vo. 195, Pt 1, Jul. 1999, pp. 10-16.

(Continued)

*Primary Examiner* — Michael A Lyons
(74) *Attorney, Agent, or Firm* — Opticus IP Law PLLC

(57) ABSTRACT

High-resolution, common-path interferometric imaging systems and methods are described, wherein a light source generates and directs light toward a sample from different directions. An optical imaging system collects the resultant scattered and unscattered components. A variable phase shifting system adjusts the relative phase of the components. The interfered components are sensed by an image sensing system. The process is repeated multiple times with different phase shifts to form corresponding multiple electronic signals representative of raw sample images, which are processed by a signal processor to form a processed image. Multiple processed images, each corresponding to a different illumination azimuth angle, are combined to extend the system resolution.

23 Claims, 18 Drawing Sheets

(56) References Cited

U.S. PATENT DOCUMENTS

| | | | |
|---|---|---|---|
| 2006/0158659 | A1 | 7/2006 | De Lega et al. |
| 2006/0215174 | A1 | 9/2006 | Dubois |
| 2008/0007726 | A1 | 1/2008 | Fairly et al. |
| 2008/0024766 | A1 | 1/2008 | Mieher et al. |
| 2008/0088849 | A1 | 4/2008 | De Lega et al. |
| 2008/0221814 | A1 | 9/2008 | Trainer |
| 2008/0266547 | A1 | 10/2008 | Clark et al. |
| 2008/0291465 | A1 | 11/2008 | Lorraine et al. |
| 2009/0296096 | A1 | 12/2009 | Jeong |
| 2010/0134786 | A1 | 6/2010 | De Lega et al. |

OTHER PUBLICATIONS

Gustafsson, "Wide-field fluorescence imaging wth theoretically unlimited resolution," PNAS Sep. 13, 2005, vol. 102, No. 37 pp. 13081-13086.

Popescu et al, "Fourier phase microscopy for investigation of biological structures and dynamics," Opt. Lett., vol. 29, No. 21, Nov. 24, 2004, pp. 2503-2505.

Cuche et al, "Simultaneous amplitude-contrast and quantitative phase contrast microscopy by numerical reconstruction of Fresnel off-axis holograms," App. Opt. vol. 38, No. 34, Dec. 1, 1999, pp. 6994-7001.

Gustafson, "Surpassing the lateral resolution limit by a factor of two using structured illumination microscopy," Journal of Microscopy, vol. 198, pt. 2, May 2000 pp. 82-87.

Kadono et al., "Phase shifting common path interferometer using a liquid-crystal phase modulator," Optics Communications 110 (1994) pp. 391-400.

Jesacher et al., "Spiral inteferogram analysis," J. Opt. Soc. Am. A vol. 23, No. 6, Jul. 2006, pp. 1400-1409.

Gazit et al., "Super-resolution and reconstruction of sparse subwavelength images," Optics Express, vol. 17, No. 26, Dec. 12, 2009, pp. 23920-23946.

Hobbs, Philip, "Building Electro-Optical Systems: Making it all work," John Wiley & Sons, Inc., 2000, pp. 30-32.

Azzam, R. M. A. et al., "Ellipsometry and Polarized Light," Elsevier Science B. V., 1999, pp. 72-84.

\* cited by examiner

HIGH-RESOLUTION, COMMON-PATH INTERFEROMETRIC IMAGING SYSTEMS AND METHODS

CROSS-REFERENCE TO RELATED APPLICATIONS

This patent application claims the benefit of U.S. Provisional Ser. No. 61/277,506, filed Sep. 25, 2009 and of U.S. Provisional Ser. No. 61/339,324, filed Mar. 3, 2010, each of which is incorporated by reference herein.

FIELD

This disclosure relates to imaging systems, and in particular relates to common-path interferometric imaging systems, and more particularly relates to high resolution, common-path interferometric imaging systems and methods.

BACKGROUND

An image-forming optical field carries both amplitude and phase information. However, conventional imaging systems record only the amplitude information and the phase information is lost. This limits the capability and the range of applications of conventional imaging technologies.

Conventional imaging systems do not fully utilize the unscattered transmitted or reflected light for the noiseless amplification of the weak image-forming field. This makes conventional imaging systems unsuitable for some tasks.

Phase-contrast microscopes perform a phase-to-intensity conversion to render phase objects visible. However, they can determine neither the phase nor the true amplitude of the image-forming field. Interferometers can determine both the phase and the amplitude of an optical field. However, conventional interferometers do not provide high enough spatial resolution to be used for imaging.

Some special interferometers such as the Linnik interferometer can determine both the phase and the amplitude with high spatial resolution and therefore can in principle be used for imaging. However, they are unstable because the probe beam and reference beam take separate paths to the image sensor.

The following references set forth techniques for extending phase-contrast microscopy and use a phase-stepping method to extract phase information of the sample: A. Y. M. Ng, C. W. See & M. G. Somekh "Quantitative optical microscope with enhanced resolution using a pixilated liquid crystal spatial light modulator" Journal of Microscopy, Vol. 214, Pt 3 June 2004, pp. 334-340, Gabriel Popescu, Lauren P. Deflores, Joshua C. Vaughan, et al "Fourier phase microscopy for investigation of biological structures and dynamics", U.S. Pat. No. 7,365,858 and U.S. Application Publication No. 2005/0105097 A1. However, these references do not show how to extract both phase and amplitude information from the measured image data, thus limiting their capability and applications.

International Patent Application Publication No. WO 2009/149103 A1, entitled "Interferometric Defect Detection and Classification," describes apparatuses and methods for defect detection and classification using a high-resolution common-path interferometric imaging system. However, it does not explicitly show how the apparatus can be used for imaging. In particular, it does not show how to remove the effects of aberrations and how to achieve a higher spatial resolution than conventional imaging techniques.

SUMMARY

Aspects of the disclosure are directed to high-resolution, common-path interferometric imaging systems and methods. Example systems include an illumination (light) source for generating light, which may include wavelengths as short as EUV (13.5 nm) and wavelengths as long as 10 microns in the far infrared, directed toward the sample. The system also includes an optical imaging system for collecting a portion of the light from the sample. The light portion includes a scattered light component that is predominantly scattered or diffracted by the sample and that constitutes an image-forming field, and an unscattered component of the light that is predominantly undiffracted, or unscattered, and transmitted or reflected by the sample. The system further includes a phase shifting system that adjusts the relative phase of the scattered component and the unscattered component. The system also includes a sensing system that measures the intensity of the combined (interfered) scattered and unscattered components. The system further includes a signal processor configured to determine from the outputs of the sensing system both the amplitude and the phase of the image-forming field. The unscattered component alone cannot form an image because it does not carry any image information. All image information is carried by the scattered component. Therefore, the scattered component is the image-forming field. The two terms "image-forming field" and "scattered component" have the same meaning and are used interchangeably herein.

The phase and amplitude of the image-forming optical field are determined by taking multiple intensity measurements with a different phase shift between the unscattered and scattered components for each measurement.

In some embodiments, the unscattered component is utilized for the noiseless amplification of the weak image-forming field.

In some embodiments, the relative phase between the unscattered and scattered components is set to a value that optimizes the signal-to-noise ratio or the quality of the image.

In some embodiments, the aberrations in the complex amplitude of the image-forming field due to an imperfect imaging system are corrected by removing the low-order frequency components in the phase distribution of the image-forming field in the pupil plane.

In some embodiments, distortion in the image is corrected by rescaling the image point-by-point.

In some embodiments, both the aberrations and distortions in the complex amplitude of the image-forming field due to an imperfect imaging system are corrected.

In some embodiments, the spatial resolution is enhanced through a pupil synthesis technique.

In some embodiments, an accurate sample positioning system is provided to accurately determine the positions of the image features of interest or locate features of interest that have been located previously.

In some embodiments a pattern recognition system, modified so as to employ both phase and amplitude in the recognition process, may be used to locate and identify specific image components In some embodiments the operator may exercise complete control over how a picture containing phase and amplitude components is displayed using color and brightness.

BRIEF DESCRIPTION OF THE DRAWINGS

The inventive body of work disclosed herein will be readily understood by referring to the following detailed description in conjunction with the accompanying drawings, in which.

DETAILED DESCRIPTION

Figure 1A:
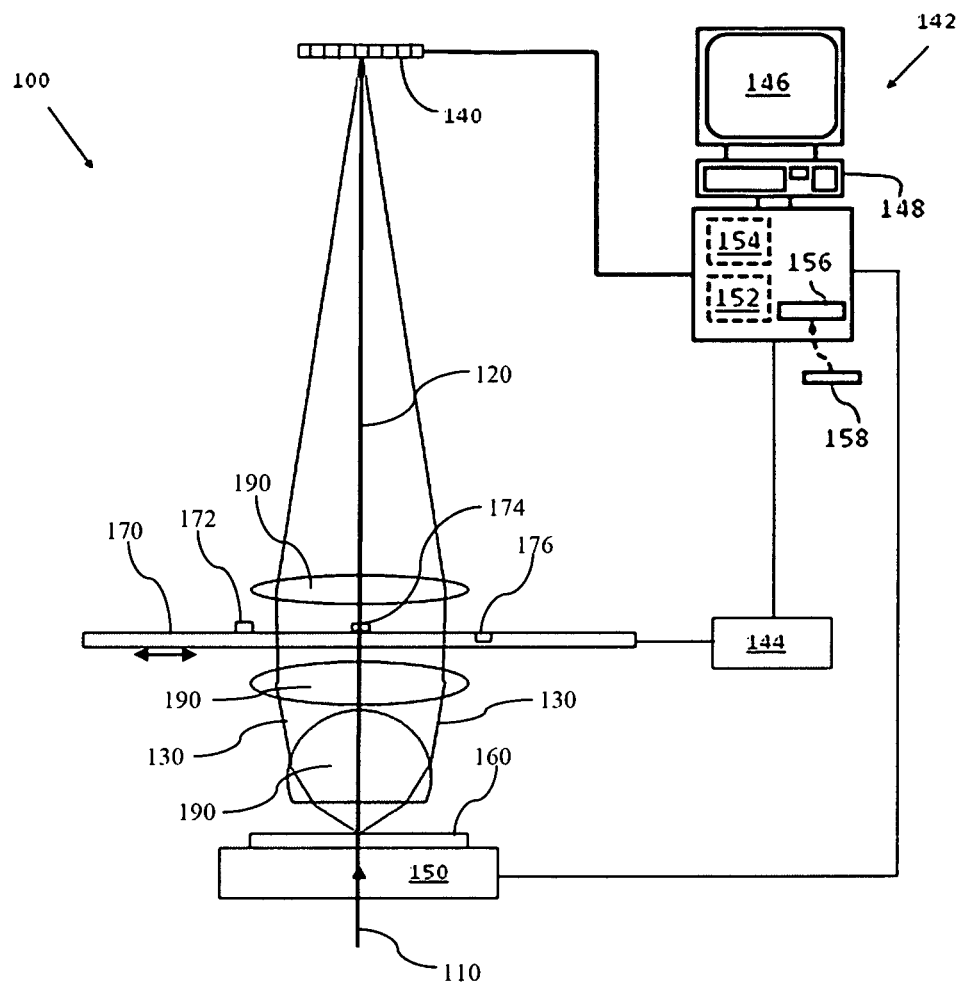
FIG. 1A shows an example of a high-resolution common-path interferometric imaging system employed in transmission mode, according to some embodiments.

A detailed description of the inventive body of work is provided below. While several embodiments are described, it should be understood that the inventive body of work is not limited to any one embodiment, but instead encompasses numerous alternatives, modifications, and equivalents, as well as combinations of features from the different embodiments. In addition, while numerous specific details are set forth in the following description in order to provide a thorough understanding of the inventive body of work, some embodiments can be practiced without some or all of these details. Moreover, for the purpose of clarity, certain technical material that is known in the related art has not been described in detail in order to avoid unnecessarily obscuring the inventive body of work.

The word "sample" as used herein simply means the object under examination. Therefore, the two words "object" and "sample" are used synonymously herein.

Also, the word "image" and "picture' are used synonymously herein.

The optical field can be described with complex amplitudes. Complex amplitudes can be conveniently represented in a Cartesian or in a polar coordinate system in a complex plane. It is represented by real and imaginary parts in a Cartesian coordinate system and amplitude and phase in a polar coordinate system. Therefore, the three phrases: "complex amplitude", "real and imaginary parts," and "amplitude and phase" are equivalent to each other as used herein, and the three terms are treated equivalently and can be exchanged with one another.

Also, the word "light" or "optical field" is used as shorthand for electromagnetic radiation having a relatively wide range of possible wavelengths, as discussed below. In addition, the unscattered component of transmission or reflection in practice is "substantially unscattered," meaning that it includes not only unscattered transmitted or reflected light but can also include a relatively small amount of scattered or diffracted light.

I. Theory

Starting from first principles, when a ray of light with a narrow temporal frequency bandwidth hits a sample, the light is either absorbed, unscattered (transmitted or reflected or undiffracted) or scattered (or diffracted) by the sample. The light that is collected by the imaging system can be decomposed into several electrical field components. Each field component of the light is defined as follows.

$b \equiv |b|\exp(i\phi_b)$; Complex amplitude of the unscattered component, where $\phi_b$ is the phase of unscattered component which can be set to zero without losing the generality of the image equation, $a \equiv |a|\exp(i(\phi_a+\phi_b)) \equiv (a_x+ia_y)\exp(i\phi_b)$; Complex amplitude of the portion of the light ray scattered or diffracted by the sample whose polarization is the same as that of b, and where $\phi_a$ is the phase of a relative to the phase of b, and $a_x$ and $a_y$ are respectively the parallel and perpendicular components of a with respect to the direction of b in the complex plane. Thus, $a_x$ and $a_y$ become the real and imaginary components of a respectively when the real axis is oriented to the direction of b. a is the main image-forming field whose amplitude and phase are to be determined using the technique disclosed herein.

$q \equiv |q| \exp(i(\phi_q + \phi_b))$; Complex amplitude of the portion of the light scattered by the sample whose polarization is orthogonal to that of b. q does not interfere with b due to the orthogonality of its polarization to that of b. Therefore, $\phi_q$ does not play any role in the imaging process and consequently can be set to any value without losing the generality of the image equation.

$g \equiv |g| \exp(i(\phi_g + \phi_b))$; Complex amplitude of any stray light present. Stray light is undesirable non-image-forming light, which is generated by unwanted reflections from lens surfaces and mechanical components. It is assumed herein that the path length of g is so much different from that of b that g and b do not interfere with each other in the image plane. Therefore, $\phi_g$ does not play any role in the imaging process and consequently can be set to any value without losing the generality of image equation.

Note that, in imaging, light of narrow temporal frequency bandwidth can be treated like the light of a single temporal frequency with the same intensity. This is not only intuitively correct but can also be easily proved mathematically. The light intensity that an image sensor detects can be expressed as follows.

The light intensity, I, detected by a detector element at the image plane is the sum of the squares of the electric field amplitudes for the unscattered, scattered and stray light components and is given by:

$$I \equiv |b+a|^2 + |q|^2 + |g|^2 \quad (1)$$

$$= |b|^2 + |g|^2 + D + (ba^* + b^*a) \quad (1a)$$

$$= |b|^2 + |g|^2 + D + 2|b||a|\cos(\varphi_a) \quad (1b)$$

$$= |b|^2 + |g|^2 + D + 2|b|a_x \quad (1c)$$

where $D \equiv |a|^2 + |q|^2$; This is known as the dark field term $\quad (1d)$ b* and a* are the complex conjugates of b and a respectively.

Equation (1d) represents the dark field term because it exists even if the unscattered component is completely blocked off. The intensity of the unscattered component and the stray light component, $|b|^2 + |g|^2$, can be measured and subtracted out from the raw image intensity, I, during image processing in order to increase the visibility of the image. Then, $\Delta I$, the image intensity after the subtraction, becomes $$\Delta I \equiv I - |b|^2 - |g|^2 \quad (2)$$

$$= |a|^2 + |q|^2 + 2|b||a|\cos(\varphi_a) = D + 2|b||a|\cos(\varphi_a) \quad (2a)$$

$$= |a|^2 + |q|^2 + 2|b|a_x = D + 2|b|a_x \quad (2b)$$

All the subsequent equations can be expressed equivalently using either I or $\Delta I$. The conversion between the two expressions is straightforward so that only one expression will usually be presented for each equation herein.

The unscattered component, b, is separated out in equation (1a) because it can be physically separated from other field components at the pupil plane. Note that all complex amplitudes are functions of position on the sample. The equations hold for each and every point in the image. Additionally, only relative phases between the unscattered and scattered components matter. Therefore, the absolute phase of the unscattered component, $\phi_b$, does not play any role and can be set to zero without losing generality. Also notice that if $\phi_b$ is set to zero, the complex amplitude of the unscattered component defines the direction of the real axis of the complex plane coordinate system used herein.

The optical path length difference of the stray light with respect to the unscattered component is assumed to be larger than the coherence length of the illumination light. Therefore, stray light is added incoherently, without considering its relative phase, in the equation (1).

Equation (1b) shows that the image intensity is composed of not only an interference term, $2|b||a|\cos(\phi_a)$, which is needed to determine both the amplitude and phase of the scattered component, but also other terms represented by D in equation (1b), which are not useful for the determination of the amplitude and phase of the scattered component.

The interference term has a remarkable property; the scattered component, the image-forming field, is amplified by the unscattered component in a noiseless fashion. This remarkable property is described in detail in WO 2009/149103 A1 "Interferometric Defect Detection and Classification" and Philip C. D. Hobbs. "Building Electro-Optical Systems; Making it all work," John Wiley & Sons, Inc., 2000, pp 30-32 and p 123, which are incorporated by reference herein. Noiseless amplification by the unscattered component is important for the handling of weak image-forming fields. It allows a reliable determination of the amplitude and phase of even a very weak image-forming field. It also allows a weak image-forming field to form a clearer image after the subtraction of background.

High noiseless amplification benefits from a strong unscattered component. Therefore, an unattenuated strong unscattered component is generally preferred herein. This is the opposite of conventional imaging where the unscattered component is either blocked off or severely attenuated to enhance the contrast of the raw images. In the systems and methods disclosed herein, the unscattered component should be attenuated only when the dynamic range of the image sensor is too small for the application.

The interference term $2|b||a|\cos(\phi_a)$, in equation (1b) is not the whole image-forming field. It is only the projection of the image-forming field onto the direction of the unscattered component in the complex plane of field representation. Consequently, in order to determine both the amplitude and phase of the image-forming field unambiguously, two more equations are needed. These equations can be generated by shifting the relative phase between the unscattered and scattered components. The relative phase can be changed by shifting either the phase of the unscattered component or the phase of the scattered component. However, it is usually easier to shift the phase of the unscattered component because the etendue of the unscattered component is much smaller than that of the scattered component. If the phase shifts are introduced to the unscattered component and are called $\theta_1$ and $\theta_2$, then the unscattered component with a respective phase shift of zero, $\theta_1$ and $\theta_2$ is expressed as follows.

$$b_0 \equiv b = |b|\exp(i\phi_b) \tag{3}$$

$$b_1 \equiv |b|\exp(i(\phi_b+\theta_1)) \tag{4}$$

$$b_2 \equiv |b|\exp(i(\phi_b+\theta_2)) \tag{5}$$

Then, the image intensities for the three cases are expressed as follows:

$$I_0 \equiv |b_0 + a|^2 + |q|^2 + |g|^2 \tag{6}$$

$$= |b|^2 + |g|^2 + D + 2|b|a_x \tag{6a}$$

$$I_1 \equiv |b_1 + a|^2 + |q|^2 + |g|^2 \tag{7}$$

$$= |b|^2 + |g|^2 + D + 2|b|(a_x\cos(\theta_1) + a_y\sin(\theta_1)) \tag{7a}$$

$$I_2 \equiv |b_2 + a|^2 + |q|^2 + |g|^2 \tag{8}$$

$$= |b|^2 + |g|^2 + D + 2|b|(a_x\cos(\theta_2) + a_y\sin(\theta_2)) \tag{8a}$$

The equations, (6a), (7a) and (8a) can be solved for the real and imaginary parts of the scattered component and the rest terms. The results are as follows.

$$2|b|a_x = \frac{I_1\sin(\theta_2) - I_2\sin(\theta_1) - I_0(\sin(\theta_2) - \sin(\theta_1))}{\sin(\theta_2 - \theta_1) - (\sin(\theta_2) - \sin(\theta_1))} \tag{9}$$

$$2|b|a_y = \frac{1}{\sin(\theta_2 - \theta_1)} \tag{10}$$

$$\left\{\begin{array}{l} -\left[\cos(\theta_2) + \frac{\sin(\theta_2)(\cos(\theta_2) - \cos(\theta_1))}{\sin(\theta_2 - \theta_1) - (\sin(\theta_2) - \sin(\theta_1))}\right]I_1 + \\ \left[\cos(\theta_1) + \frac{\sin(\theta_1)(\cos(\theta_2) - \cos(\theta_1))}{\sin(\theta_2 - \theta_1) - (\sin(\theta_2) - \sin(\theta_1))}\right]I_2 + \\ (\cos(\theta_2) - \cos(\theta_1))\left[1 + \frac{(\sin(\theta_2) - \sin(\theta_1))}{\sin(\theta_2 - \theta_1) - (\sin(\theta_2) - \sin(\theta_1))}\right]I_0 \end{array}\right\}$$

$$D = \frac{I_0\sin(\theta_2 - \theta_1) - I_1\sin(\theta_2) + I_2\sin(\theta_1)}{\sin(\theta_2 - \theta_1) - (\sin(\theta_2) - \sin(\theta_1))} - |b|^2 - |g|^2 \tag{11}$$

$$= \frac{\Delta I_0\sin(\theta_2 - \theta_1) - \Delta I_1\sin(\theta_2) + \Delta I_2\sin(\theta_1)}{\sin(\theta_2 - \theta_1) - (\sin(\theta_2) - \sin(\theta_1))} \tag{11a}$$

If $\theta_1 = -\theta_2 = \theta \neq 0$, then, equations (9), (10), and (11) reduce to the following equations:

$$2|b|a_x = \frac{(2I_0 - I_1 - I_2)\sin(\theta)}{2\sin(\theta) - \sin(2\theta)} \tag{12}$$

$$2|b|a_y = \frac{(I_1 - I_2)\cos\theta}{\sin(2\theta)} \tag{13}$$

$$D = \frac{(I_1 + I_2)\sin(\theta) - I_0\sin(2\theta)}{2\sin(\theta) - \sin(2\theta)} - |b|^2 - |g|^2 \tag{14}$$

$$= \frac{(\Delta I_1 + \Delta I_2)\sin(\theta) - \Delta I_0\sin(2\theta)}{2\sin(\theta) - \sin(2\theta)} \tag{14a}$$

There are several good choices for $\theta_1$ and $\theta_2$ values. One of the good choices is:

$$\theta_1 = -\theta_2 = \frac{2\pi}{3}.$$

If $$\theta_1 = -\theta_2 = \frac{2\pi}{3},$$

then, equations (12), (13) and (14) further reduce to the following equations:

$$2|b|a_x = \frac{2I_0 - I_1 - I_2}{3} \tag{15}$$

$$2|b|a_y = \frac{I_1 - I_2}{\sqrt{3}} \tag{16}$$

$$D = \frac{I_0 + I_1 + I_2}{3} - |b|^2 - |g|^2 \tag{17}$$

$$= \frac{\Delta I_0 + \Delta I_1 + \Delta I_2}{3} \tag{17a}$$

$I_a$, the amplified intensity of the image-forming field, for this case has the following simple expression:

$$I_a \equiv (2|b|a_x)^2 + (2|b|a_y)^2 \tag{18}$$

$$= \frac{4}{9}(I_0^2 + I_1^2 + I_2^2 - I_0 I_1 - I_1 I_2 - I_2 I_0)$$

$$= \frac{2}{9}[(I_0 - I_1)^2 + (I_1 - I_2)^2 + (I_2 - I_0)^2]$$

where $I_a$ is a raw intensity of the image-forming field. Its magnitude depends not only on the intensity of the illumination light but also on the intensity of the unscattered component. Therefore, in order to make the image intensity more consistent, $I_a$ should be normalized against the intensities of the illumination light beam and the unscattered component.

The intensity of the unscattered component can vary significantly over the whole field. An exact determination of the variation of the unscattered component across the field requires a measurement of the unscattered component at the image plane, which requires a complete blocking of the scattered component. This additional measurement can reduce the system throughput. Fortunately, exact values of the local intensity of the unscattered component are not needed for most applications. Approximate values are fine for normalization purposes. Local intensity values of the unscattered component can be approximated by the local average of the total light intensity in most cases. Therefore, the raw amplified intensity of the image-forming field, $I_a$ can be properly normalized as follows:

$$I_a' \approx \frac{2}{9} \frac{\lfloor(I_0 - I_1)^2 + (I_1 - I_2)^2 + (I_2 - I_0)^2\rfloor}{I_{ill} \cdot I_{local}} \tag{19}$$

where $I_{ill}$ is the intensity of the illumination at the sample plane.

$I_{local}$ is the local average of the total light intensity at the image plane $I'_a$ is the normalized intensity of the image-forming field. $I_{ill}$ normalizes $|a|^2$ and $I_{local}$ normalizes $|b|^2$.

A numerical deconvolution of the intensity of the image-forming field with the finite width of detector element can be applied in order to get a more accurate intensity distribution across the field.

The phase of the image-forming field, $\phi_a$, relative to the unscattered component, becomes:

$$\varphi_a = \tan^{-1}\left(\frac{a_y}{a_x}\right) = \tan^{-1}\left(\frac{\sqrt{3}(I_1 - I_2)}{2I_0 - I_1 - I_2}\right) \quad (20)$$

A more meaningful phase value is the difference between $\phi_a$ and the reference phase value, which is determined during the optical system calibration process. The reference phase value should be zero all over the field if the imaging system is aberration-free and the amount of phase shift each phase shifting element introduces is precisely known. However, real systems are neither perfect nor can they be characterized with infinite precision. Therefore, small but non-zero reference phase values are expected in real systems and need to be determined to achieve better performance of the system. The reference phase value is the piston term in the polynomial expansion of aberration and can therefore be determined readily during the measurement of the aberrations of the imaging system, which will be discussed in a later section, Aberration Correction.

In many cases, it may be hard to introduce specific phase values. However, this is not a problem as long as we know the value of the phases we introduce, we can use more general equations (9) through (11) to get the complex amplitude and the dark field intensity of the image-forming field.

As stated previously, in general it takes at least three sample images in order to determine the complex amplitude of the image-forming field completely. However, if the dark field part of the whole signal is negligible compared with the interference part, then two sample images suffice to determine the complex amplitude of the image-forming field. This can be seen from equations (6a) and (7a). If we ignore the dark field part in the equations and set $$\theta_1 = \pm \frac{\pi}{2},$$

then, those equations give $$2|b|a_x \approx I_0 - |b|^2 - |g|^2 = \Delta I_0 \quad (21)$$

$$2|b|a_y \approx \pm(I_1 - |b|^2 - |g|^2) = \pm\Delta I_1 \quad (22)$$

The intensity of the amplified image-forming field, $I_a$, becomes $$I_a \equiv (2|b|a_x)^2 + (2|b|a_y)^2 \quad (23)$$

$$\approx \Delta I_0^2 + \Delta I_1^2$$

The normalized intensity of the amplified image-forming field, $I_a'$, becomes $$I'_a \approx \frac{\Delta I_0^2 + \Delta I_1^2}{I_{ill} \cdot I_{local}} \quad (24)$$

If the unscattered component is strong and the image sensor has a large dynamic range, then we can boost the interference part of the optical field by a large amount using the strong unscattered component. In this case, the dark field part of the whole field can be so small that we may be able to use the two image method to speed up the whole interferometric imaging process.

A method of four sample images with a different phase value for each image can also be used. A simple choice for the four phase values of the unscattered component is $0$, $\pi$, $$\frac{\pi}{2}$$

and $$-\frac{\pi}{2}.$$

If we take a picture of the sample image four times with $0$, $\pi$, $$\frac{\pi}{2}$$

and $$-\frac{\pi}{2}$$

phase values of the unscattered component, then:

$$b_0 \equiv b = |b|\exp(i\varphi_b) \quad (25)$$

$$b_1 \equiv |b|\exp(i(\varphi_b + \pi)) \quad (26)$$

$$b_2 \equiv |b|\exp\left(i\left(\varphi_b + \frac{\pi}{2}\right)\right) \quad (27)$$

$$b_3 \equiv |b|\exp\left(i\left(\varphi_b - \frac{\pi}{2}\right)\right) \quad (28)$$

The intensity of each image becomes:

$$\Delta I_0 = I_0 - |b|^2 - |g|^2 = |a|^2 + |q|^2 + 2|b|a_x \quad (29)$$

$$\Delta I_1 = I_1 - |b|^2 - |g|^2 = |a|^2 + |q|^2 - 2|b|a_x \quad (30)$$

$$\Delta I_2 = I_2 - |b|^2 - |g|^2 = |a|^2 + |q|^2 + 2|b|a_y \quad (31)$$

$$\Delta I_3 = I_3 - |b|^2 - |g|^2 = |a|^2 + |q|^2 - 2|b|a_y \quad (32)$$

The real and imaginary parts of the complex amplitude of the amplified image-forming field at the image plane become:

$$2|b|a_x = \frac{I_0 - I_1}{2} = \frac{\Delta I_0 - \Delta I_1}{2} \quad (33)$$

-continued $$2|b|a_y = \frac{I_2 - I_3}{2} = \frac{\Delta I_2 - \Delta I_3}{2} \quad (34)$$

The dark field term becomes;

$$D = \frac{\Delta I_0 + \Delta I_1}{2} = \frac{\Delta I_2 + \Delta I_3}{2} = \frac{\Delta I_0 + \Delta I_1 + \Delta I_2 + \Delta I_3}{4} \quad (35)$$

The intensity of the amplified image-forming field, $I_a$, for this case has the following simple expression:

$$I_a \equiv (2|b|a_x)^2 + (2|b|a_y)^2 \quad (36)$$

$$= \frac{1}{4}[(\Delta I_0 - \Delta I_1)^2 + (\Delta I_2 - \Delta I_3)^2]$$

The normalized intensity of the image-forming field becomes:

$$I'_a \approx \frac{1}{4} \frac{[(\Delta I_0 - \Delta I_1)^2 + (\Delta I_2 - \Delta I_3)^2]}{I_{ill} \cdot I_{local}} \quad (37)$$

$\phi_a$, the phase of the image-forming field relative to the unscattered component, becomes $$\varphi_a = \tan^{-1}\left(\frac{a_y}{a_x}\right) = \tan^{-1}\left(\frac{\Delta I_2 - \Delta I_3}{\Delta I_0 - \Delta I_1}\right) \quad (38)$$

This four image method provides simpler equations. However, its main drawback is that the relative phase angle between the image-forming field and the unscattered component can be as large as 45°. Notice that the maximum relative phase angle for the three-image method is only 30°. This fact can make this four-image method perform poorer for some objects than the three image method. In order to achieve better performance than the three image method, different phase values than $\{0, \pi, \pi/2$ and $-\pi/2\}$
can be chosen. Possible different choices are $$\left\{0, \frac{\pi}{4}, \frac{\pi}{2} \text{ and } \frac{3\pi}{4}\right\}, \left\{\pm\frac{\pi}{8}, \pm\frac{3\pi}{8}\right\},$$

etc. However, these other choices involve the use of a regression method to determine the complex amplitude of the image-forming field and make the analytical expression of the image-forming field more complicated. See the following paragraphs for a general expression of the complex amplitude of the image-forming field. Another drawback of the four-image method is reduced throughput compared with the three-image method thanks to the extra sample image needed.

More independent image data leads to a better signal-to-noise ratio or higher quality in the final processed or reconstructed image. Therefore, to increase the signal-to-noise ratio or the quality of the reconstructed image, a sample image can be taken more than four times with a different phase setting of the unscattered component for each image taken. In this case, the amount of data is more than that needed to determine uniquely the complex amplitude of the image-forming field. Therefore, a regression method should be adopted to determine the complex amplitude of the image-forming field. There are many different regression methods available with known pros and cons. One of the most popular methods is the least-square regression. It is the preferred choice if the noise is random and it also allows an analytical approach for the current case. Analytical regression is important because it can save a lot of computation time. Other regression methods can be more suitable if the noise is not random but they usually do not allow analytical approaches. Therefore, only the least-square regression is presented here.

Let us assume that sample image is taken N times with a different phase setting for each image taken, then, $\Delta I_n^{(0)}$, the theoretical intensity of the nth image, is expressed as follows:

$$\Delta I_n^{(0)} \equiv I_n^{(0)} - |b|^2 - |g|^2 = D + 2|b|(a_x \cos(\theta_n) + a_y \sin(\theta_n)) \quad (39)$$

where $D \equiv |a|^2 + |q|^2$: dark field term  (40)

The error function is defined as follows in a least-square regression.

$$E = \sum_{n=0}^{N-1} (\Delta I_n - \Delta I_n^{(0)})^2 \quad (41)$$

where $\Delta I_n$ is the intensity of nth actual image taken with the unscattered component and the stray light removed and $\Delta I_n^{(0)}$ is the nth theoretical image intensity with the unscattered component and the stray light removed as shown in equation (39)

We have to find D, $a_x$ and $a_y$ values that minimize the error function. The slopes of the error function with respect to D, and with respect to $a_x$ and with respect to $a_y$ all become zero at its minimum. Therefore, the solution satisfies following three equations:

$$\frac{-1}{2}\frac{\partial E}{\partial D} = \sum_{n=0}^{N-1}(\Delta I_n - \Delta I_n^{(0)}) = 0 \quad (42)$$

$$= \sum_{n=0}^{N-1} \Delta I_n - \sum_{n=0}^{N-1}[D + 2|b|(a_x\cos(\theta_n) + a_y\sin(\theta_n))]$$

$$= \sum_{n=0}^{N-1} \Delta I_n - ND - 2|b|\sum_{n=0}^{N-1}(a_x\cos(\theta_n) + a_y\sin(\theta_n)),$$

$$\frac{-1}{4|b|}\frac{\partial E}{\partial a_x} = \sum_{n=0}^{N-1}\cos(\theta_n)(\Delta I_n - \Delta I_n^{(0)}) = 0 \quad (43)$$

$$= \sum_{n=0}^{N-1}\Delta I_n\cos(\theta_n) - \sum_{n=0}^{N-1}[D\cos(\theta_n) + 2|b|(a_x\cos^2(\theta_n) + a_y\sin(\theta_n)\cos(\theta_n))]$$

$$= \sum_{n=0}^{N-1}\Delta I_n\cos(\theta_n) - D\sum_{n=0}^{N-1}\cos(\theta_n) -$$

$$|b|a_x\left[N + \sum_{n=0}^{N-1}\cos(2\theta_n)\right] - |b|a_y\sum_{n=0}^{N-1}\sin(2\theta_n)$$

and $$\frac{-1}{4|b|}\frac{\partial E}{\partial a_y} = \sum_{n=0}^{N-1} \sin(\theta_n)(\Delta I_n - \Delta I_n^{(0)}) = 0 \quad (44)$$

$$= \sum_{n=0}^{N-1} \Delta I_n \sin(\theta_n) - \sum_{n=0}^{N-1} [D\sin(\theta_n) + 2|b|(a_x\sin(\theta_n)\cos(\theta_n) + a_y\sin^2(\theta_n))]$$

$$= \sum_{n=0}^{N-1} \Delta I_n \sin(\theta_n) - D\sum_{n=0}^{N-1} \sin(\theta_n) - |b|a_x \sum_{n=0}^{N-1} \sin(2\theta_n) - |b|a_y \left[N - \sum_{n=0}^{N-1} \cos(2\theta_n)\right]$$

Then, from equation (42):

$$D = \frac{1}{N}\sum_{n=0}^{N-1} \Delta I_n - \frac{2|b|}{N}\sum_{n=0}^{N-1} (a_x \cos(\theta_n) + a_y \sin(\theta_n)) \quad (45)$$

By substituting equation (45) into equations (43) and (44):

$$\frac{1}{4|b|}\frac{\partial E}{\partial a_x} = A - B|b|a_x = C|b|a_y = 0 \quad (46)$$

$$\frac{-1}{4|b|}\frac{\partial E}{\partial a_y} = A' - C|b|a_x - B'|b|a_y = 0 \quad (47)$$

where $A \equiv \sum_{n=0}^{N-1} \Delta I_n \cos(\theta_n) - \frac{1}{N}\left(\sum_{n=0}^{N-1} \Delta I_n\right)\left(\sum_{n=0}^{N-1} \cos(\theta_n)\right)$ (48)

$$B \equiv N + \sum_{n=0}^{N-1} \cos(2\theta_n) - \frac{2}{N}\left(\sum_{n=0}^{N-1} \cos(\theta_n)\right)^2 \quad (49)$$

$$C \equiv \sum_{n=0}^{N-1} \sin(2\theta_n) - \frac{2}{N}\left(\sum_{n=0}^{N-1} \cos(\theta_n)\right)\left(\sum_{n=0}^{N-1} \sin(\theta_n)\right) \quad (50)$$

$$A' \equiv \sum_{n=0}^{N-1} \Delta I_n \sin(\theta_n) - \frac{1}{N}\left(\sum_{n=0}^{N-1} \Delta I_n\right)\left(\sum_{n=0}^{N-1} \sin(\theta_n)\right) \quad (51)$$

$$B' \equiv N - \sum_{n=0}^{N-1} \cos(2\theta_n) - \frac{2}{N}\left(\sum_{n=0}^{N-1} \sin(\theta_n)\right)^2 \quad (52)$$

From equations (46) and (47):

$$|b|a_x = \frac{AB' - A'C}{BB' - C^2} \quad (53)$$

$$|b|a_y = \frac{A'B - AC}{BB' - C^2} \quad (54)$$

Equations (53) and (54) are the general best solutions for the complex amplitude of the amplified image-forming field. By substituting equations (53) and (54) into equation (45):

$$D = \frac{1}{N}\sum_{n=0}^{N-1} \Delta I_n - \quad (55)$$

$$\frac{2}{N}\left[\left(\frac{AB' - A'C}{BB' - C^2}\right)\left(\sum_{n=0}^{N-1} \cos(\theta_n)\right) + \left(\frac{A'B - AC}{BB' - C^2}\right)\left(\sum_{n=0}^{N-1} \sin(\theta_n)\right)\right]$$

The absolute amplitude and phase of the image-forming field can be computed quickly from equations (53) and (54). Equation (55) can be normalized with illumination intensity and used to evaluate the quality of the dark field image. By evaluating the relative intensity of the dark field image with respect to the noise level, we can tell if the dark field mode of operation will work well or not.

The general equations (53) through (55) can be very useful when we want to see some specific feature in the image more clearly than other features and have some knowledge about the feature because they allow us to utilize our knowledge about the feature. For example, if we want to determine the complex amplitude of a specific feature in the image accurately and we know the complex amplitude value of the feature approximately, we can choose the phase values of the phase shifter more densely around the parallel and antiparallel directions to the complex amplitude of the feature in the complex plane. Even if we do not utilize our knowledge about features in the image, the general equations (53) through (55) can still be very useful. For example, the phase values available from step-variable phase shifters such as those made by thin film deposition may not exactly match the specific values used for the derivation of non-general equations. In this case, we are forced to use the general equations.

Generally, if $N \geq 4$, we can also estimate the integrity of the image data by computing the amount of residual error after the regression. The residual error can be computed quickly by substituting equations (53), (54) and (55) into equation (41) and summing up each term in the equation. By comparing the residual error with a preset value, we can tell the soundness of the whole process. Checking the residual error is especially helpful in system trouble-shooting. It is usually the first step in a system trouble-shooting process.

Equations (53) through (55) reduce to equations (9) through (11) respectively when $N=3$.

If the phase settings are chosen to meet following condition:

$$\sum_{n=0}^{N-1} \cos(\theta_n) = \sum_{n=0}^{N-1} \sin(\theta_n) = \sum_{n=0}^{N-1} \cos(2\theta_n) = \sum_{n=0}^{N-1} \sin(2\theta_n) = 0 \quad (56)$$

(As an example, the above condition can be met if all the $\theta_n$ are chosen with even angular intervals between them.)

then:

$$A = \sum_{n=0}^{N-1} \Delta I_n \cos(\theta_n), \; A' = \sum_{n=0}^{N-1} \Delta I_n \sin(\theta_n), \; B = B' = N, \; C = 0 \quad (57)$$

and, consequently, in this case:

$$|b|a_x = \frac{A}{N} = \frac{1}{N}\sum_{n=0}^{N-1} \Delta I_n \cos(\theta_n) \quad (58)$$

$$|b|a_y = \frac{A'}{N} = \frac{1}{N}\sum_{n=0}^{N-1} \Delta I_n \sin(\theta_n) \quad (59)$$

$$D = \frac{1}{N}\sum_{n=0}^{N-1} \Delta I_n \quad (60)$$

From equations (58) and (59), $$I_{a2} \equiv (2|b|a_x)^2 + (2|b|a_y)^2 \quad (61)$$

$$= \frac{4}{N^2}\sum_{m=0}^{N-1}\sum_{n=0}^{N-1} \Delta I_m \Delta I_n \cos(\theta_m - \theta_n)$$

It is easy to see that equations (58) through (61) reduce to equations (15) through (18) respectively when N=3 and $\theta_0$=0, $$\theta_1 = -\theta_2 = \frac{2\pi}{3}.$$

They also reduce to equations (33) through (36) when N=4 and $\theta_0$=0, $\theta_1$=$\pi$, $$\theta_2 = -\theta_3 = \frac{\pi}{2}.$$

As shown above, the regression process for the determination of the complex amplitude of the image-forming field can be done analytically. Therefore, the determination of the complex amplitude of the image-forming field does not require excessive computing time even if the sample image is taken a lot more than three times in order to obtain more reliable image data. Definitely, taking more images means lower throughput. However, if the signal-to-noise ratio of each raw image is low but a high signal-to-noise ratio is needed for the reconstructed image, taking more sample images can help significantly. For example, an accurate study of the image-forming field can benefit from a supply of reconstructed image data having high signal-to-noise ratios and this can be easily obtained by taking the sample image a large number of times.

Heterodyne Mode.

If N is large and the relative phase can be changed rapidly and the raw image data can be collected rapidly, then the system can be operated in heterodyne mode. The heterodyne mode suffers less 1/f noise and so is able to provide cleaner image data generally. The heterodyne method can be implemented with relative ease in static or stepping systems, however, it is usually hard to implement in scanning systems, especially in fast scanning systems.

Contrast Enhancement.

A strong unscattered component can be used to obtain high noiseless amplification of the image-forming field. High noiseless amplification of the image-forming field leads to higher image quality or a more accurate determination of the amplitude and phase of the image-forming field. Therefore, a strong unscattered component is generally preferred. However, too strong an unscattered component can saturate the image sensor if its dynamic range is not large enough, and consequently result in undesirable image distortion. This can also lead to a deficient number of gray levels in the image. Therefore, when the dynamic range of the image sensor is saturated, the contrast of the raw image may need to be increased, and the unscattered component decreased, in order to avoid image detector distortion, which is distinctly different from imaging system distortion that arises from the design of the imaging system or imperfections in the imaging system components or their alignment.

If the object to be imaged is very faint, significant attenuation of the unscattered component along with more intense illumination light may be useful in order to get a suitably high contrast in the raw image. Alternatively attenuation can be employed along with a longer picture integration time on the detector array. In either case more photons are received from the faint object relative to the unscattered component.

One of the drawbacks of this kind of contrast enhancement technique is the large loss of light energy. In order to compensate for the energy loss due to the attenuation of the unscattered component, more light can be supplied to the illumination path or the detector signal can be integrated for a longer period of time. In many applications, neither of these options is desirable because an intense illumination beam can damage samples and a longer detector integration time will reduce throughput. Therefore, contrast enhancement must be used with care with these and other undesirable side effects in mind. Note that illuminating a larger area on the sample and employing a proportionally larger detector array can reduce the possibility of sample damage by intense illumination light while preserving throughput, but this usually requires a more expensive instrument design.

Fortunately, most actual cases do not require extreme contrast enhancement thanks to a large dynamic range of the image sensors available commercially. Moderate contrast enhancement is not only very acceptable with current practice, but also preferred, considering the need for signal amplification, the efficiency of light energy use and system throughput.

Selection of Polarization

For some cases, the signal-to-noise ratio of the image depends on the polarization states of the illumination light and/or the collected light. Therefore, it is sometimes important to select correct polarizations for the illumination and the collected light. The selection of correct polarizations can be done with intuition, theoretical modeling, numerical simulations or experimentation. However, it is usually impractical to test all the different polarization combinations because of their large number. Therefore, a good understanding of the interaction of polarized light with the sample material is preferred when trying to determine the right polarization. For example, as long as the sample does not have helical structures, the polarization choices can be limited to combinations of linear polarizations.

Aberration Correction

Actual imaging systems are not perfect and their imperfections can contribute a significant amount of aberrations to the image-forming field. Typical aberrations include piston, defocus, field curvature, astigmatism, coma, spherical aberration, etc. However, the interferometric imaging technique disclosed herein allows for complete removal of the aberrations from the complex amplitude image. Note that the piston term in the polynomial expansion of aberration cannot be ignored in the interferometric imaging technique disclosed herein because it can directly affect the phase value of the complex amplitude of the image-forming field. The description of aberrations at the image plane is somewhat complicated. However, its description at the pupil plane is simple and straightforward. Aberrations cause low order or slowly varying shapes on the wavefront, or equivalently, low frequency variations in the phase distribution at the pupil plane. In other words, if an image-forming field is not aberrated, its phase distribution or wavefront at the pupil plane should not have any low frequency wiggles even if the phase distribution, due to the object itself, is very complicated and/or highly varying across the pupil. Therefore, aberrations can be corrected by removing the low spatial frequency wiggles in the phase distribution of the image-forming field at the pupil plane. As is well known, the phase distribution of the image-forming field at the pupil plane can be obtained easily by Fourier-transforming the complex amplitude of the image-forming field at the image plane.

The removal of low spatial frequency wiggles from a wavefront or phase distribution usually requires numerical fitting of slowly varying functions, such as low order Zernike polynomials, to the original phase distribution. This kind of numerical operation can be prone to error if the fitting operation is extended to higher spatial frequencies because some components of the wavefront wiggles caused by the sample object can be misinterpreted as an optical system aberration if high frequency aberration correction is attempted. This kind of error can be avoided if the optical system aberrations that need to be corrected are known beforehand. Thus, if the aberrations of the imaging system are measured beforehand, the aberration component of the optical system can be directly subtracted from the wavefront or phase distribution of the image-forming field at the pupil plane thereby avoiding a numerical fitting operation completely. Thus, measuring the aberrations of the imaging system is still desirable even if the aberration correction can be performed without knowing the aberrations of the imaging system beforehand.

The aberrations of the imaging system can be measured using conventional methods, such phase-shifting interferometry, Hartmann test, etc. However, a more convenient way of measuring aberrations is to use the interferometric imaging system itself because it does not require any additional hardware. In the transmission mode optical system, an example test object comprises an array of pin-holes in a semi-transparent film covering the entire field of view. An array of pin-holes rather than a single pin-hole is needed because the amount of aberration usually depends on the position within the field. That is, in order to know the variation of aberrations across the field, an array of pin-holes rather than single pin-hole is needed. The film needs to be somewhat transparent in order to have a strong enough unscattered component. In a reflective mode optical system, reflective pin-dots rather than pin-holes can also be used. In this case a pin-dot is a small highly reflective area arrayed on a partially reflective background. In the reflective mode, it is also possible to employ absorbing pin-dots that have no reflectivity. In this case, the measured complex amplitude of the image-forming field is the negative of the amplitude point spread function. The interferometric imaging system and method disclosed herein can determine the complex amplitude distribution of the image of each pin-hole/pin-dot. The wavefront aberration, the aberration measured in the pupil plane, is just the Fourier-transform of the complex amplitude of a pin-hole image at the image plane. A small bright pin-dot in the reflective mode of operation is optically equivalent to a pinhole in the transmission mode of operation and a non-reflective pin-dot in the reflective mode is equivalent to an opaque pin-dot in the transmission mode of operation Therefore, the same arguments hold for either mode of operation.

The constant or piston term in the polynomial expansion of aberration in the pupil plane constitutes the reference phase value in the interferometric imaging system and originates from the uncertainty in the phase values the phase shifters introduce and its interaction with the real aberration of the imaging system. The piston term is not considered as an aberration in conventional imaging systems because it does not affect the image. However, the piston term, which generally varies across the field, needs to be known as precisely as possible for the interferometric imaging system, because it can directly affect the phase value of the complex amplitude of the image-forming field. Thus, the piston term, determined during the aberration measurement, should not be abandoned but must be kept and used as the reference phase value.

This approach to aberration correction is possible because the complex amplitude of the image-forming field can be determined using the new imaging techniques disclosed herein. Complete aberration correction is impossible in conventional imaging because the complex amplitude of the image-forming field cannot be obtained. Aberration correction is not possible using image intensity data only. The capability of aberration correction from the complex amplitude of the image-forming field is one of the important advantages of the interferometric imaging technique disclosed herein.

Imaging System Distortion Correction

Real imaging systems are never perfect either in design or in execution. At any point in the field, phase changes can be introduced in the wavefront forming the image as a result of design imperfections or fabrication errors in the lens surfaces or in the alignment of the lens elements. Generally these are called imaging system aberrations. Included in the aberration set is an aberration called distortion, which can be interpreted as a variation of the image magnification across the field. Therefore, distortion in an image can be corrected by readjusting image magnification across the whole image. In order to do that, one needs to know what kind of image distortion the imaging system creates. A straightforward way of measuring the distortion created by an imaging system is to take an image of an array of pin-holes arranged across the field in a regular fashion. The same pin-hole array used for the determination of aberrations can be used. By measuring the position of each pin-hole in the test artifact and comparing a best-fit, scaled version of these positions with the corresponding positions measured in the image, the distortion for each image point can be determined accurately and the variation of distortion across the field can be fitted to an equation. This equation can then be used to laterally shift each image point in any sample to eliminate imaging system distortion across the whole image. A slight readjustment of image intensity distribution may also be needed to conserve the energy at every point in the image.

Relationship of Complex Amplitude with Sample Physical Properties

If the sample is thick or strongly scatters the incoming light, it is hard to establish the relationship between the complex amplitude of the image-forming light and the physical properties of the sample. However, if the sample is thin and weakly scattering, a direct relationship between the complex amplitude of the image-forming light and some physical property of the sample can be established. In case of a thin sample, the relationship between the complex amplitude of image-forming field and the complex refractive index of the sample becomes:

$$a_x + i a_y \approx \exp(ik\hat{n}t) - \exp(ik\bar{n}t)$$

$$\approx ik(\hat{n}-\bar{n})t = ikt((n-\bar{n})+i(\kappa-\bar{\kappa})) = ikt(\Delta n - i\Delta\kappa) \quad (62)$$

where $a_x$=the real part of the normalized complex amplitude of the image-forming field $a_y$=the imaginary part of the normalized complex amplitude of the image-forming field $$k = \frac{2\pi}{\lambda};$$

wavenumber; $\hat{n}=n+i\kappa$; complex refractive index, where n is the real part of the complex refractive index, $\kappa$ is the imaginary part of the complex refractive index, $\overline{\hat{n}}=\overline{n}+i\overline{\kappa}$, average complex refractive index, where $\overline{n}$ is the real part of the average complex refractive index $\overline{\kappa}$ is the imaginary part of the average complex refractive index, $\Delta n=n-\overline{n}$, $\Delta\kappa=\kappa-\overline{\kappa}m$ and t=the thickness of the sample.

In equation (62), the complex amplitude of the image-forming field is normalized against the intensity of the illumination ray. That is, both the intensity and the amplitude of the illumination ray are assumed to be unity.

From equation (62), $$kt \cdot \Delta\kappa \approx -a_x \quad (62a)$$

and $$kt \cdot \Delta n \approx a_y \quad (62b)$$

The absorption coefficient is given by:

$$\alpha = 2k\kappa \quad (63)$$

where $\alpha$ is absorption coefficient.
Therefore, $$t\Delta\alpha \approx -2a_x \quad (63b)$$

In the case of a reflecting sample with low surface topology $$a_x+ia_y \approx r\exp(i2kh) - \overline{r}\exp(i2k\overline{h}) \approx (r-\overline{r})+i2k(rh-\overline{rh}) \quad (64)$$

where r=√Reflectivity; reflection coefficient
$\overline{r}$=average reflection coefficient
h=optical height or depth of surface topology
$\overline{h}$=average optical height or depth of surface topology
From equation (64), $$(r-\overline{r}) \approx a_x \quad (64a)$$

$$2k(rh-\overline{rh}) \approx a_y \quad (64b)$$

The straightforward relationships of the complex amplitude of the image-forming field with some physical properties of the sample can make the interferometric imaging technique disclosed herein very useful in a variety of applications and expands the range of applications of optical imaging technology.

II. System Configuration

Interferometric imaging systems can be configured in many different ways. Many examples include a common path and a provision for changing the relative phase between the scattered and the unscattered components.

One system configuration is shown in FIG. 1A. System 100 shown therein is for a transmission mode of operation. A light beam 110 illuminates a sample 160 and covers the whole field of view. The illumination beam 110 is usually collimated at the sample. A laser beam with a single spatial mode is preferred because it will allow a clean separation of the unscattered component 120 from the scattered component 130 at the pupil plane resulting in uncompromised system performance. It can be difficult to achieve good spatial uniformity over the whole field with single spatial mode illumination beam. However, this is usually not a problem because the spatial non-uniformity is highly static and consequently can easily be calibrated out by the image processor.

Note that the requirements on microscopy illumination are very different than those for lithography. Lithography generally requires high spatial uniformity over the whole field. However, an interferometric imaging system does not require high illumination uniformity. Rather, it requires good stability of the illumination pattern. The use of a speckle buster such as a rotating ground glass plate in the path of illumination beam is highly discouraged, because it will not only add cost but also degrade system performance by adding speckle noise and making a clean separation of the unscattered component from the scattered component impossible.

The number of temporal modes in the illumination beam can be greater than one. Actually, in most applications, a large number of temporal modes are preferred because this can reduce unwanted interferences such as coherent interference of stray or ghost light with the unscattered component.

Many different kinds of light sources can be used in the systems and methods disclosed herein. However, bright sources are preferred because they allow a clean spatial separation of the unscattered component from the scattered component at pupil conjugate planes of the optical imaging system. The brightest sources currently available are lasers. Therefore, lasers are the preferred sources for the new disclosure. Other sources like arc lamps, light emitting diodes (LED), etc, can also be used in the new disclosure.

The use of lasers as the light source can create damaging hot spots on or in some optical systems. However, this problem can be mitigated by an optical design change or by the use of damage-resistant lens materials such as specially formulated fused silica, calcium fluoride, lithium fluoride, etc.

The sample 160 scatters (or diffracts) part of the incident illumination beam 110 and either absorbs the rest or transmits it unscattered. Note that the scattered (or diffracted) and unscattered transmitted portions of the incident light are called the "scattered component" and "unscattered component," respectively herein. A high-resolution, common-path, optical system 190 collects both the scattered and unscattered components of the incident light and directs them to an image sensor 140. The unscattered component 120 alone cannot form an image. However, the scattered component 130 alone can form an image even without the unscattered component 120. Therefore, the scattered component 130 constitutes the image-forming field.

There are many different kinds of image sensors. But, two-dimensional image sensors like conventional CCD (charge-coupled device), TDI (time delay and integration), CMOS (complementary metal-oxide-semiconductor) image sensor, etc, are most appropriate for the interferometric imaging system. As shown in FIG. 1A, both the scattered and unscattered components pass through the same optical system 190. Thus, the interferometric imaging system 100 disclosed herein is a type of common path interferometer system. This feature ensures the stability of the system performance. This is because any disturbances to the common path interferometer are likely to affect both optical paths by the same amount and the relative phase difference between scattered and unscattered components is likely to be maintained.

Figure 1B:
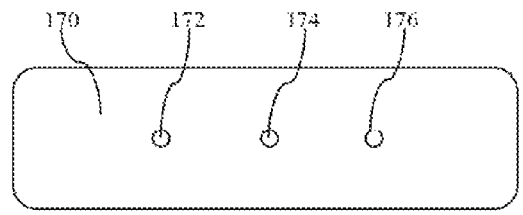
FIG. 1B shows a top view of the phase shifter shown in FIG. 1A.

The systems and methods described herein utilize a variable phase shifter 170. A variable phase shifter can be made in many different ways. However, the example system shown in FIG. 1A has a phase shifting plate 170 with multiple phase shifting elements 172, 174 and 176 each capable of changing the relative phase between the scattered and the unscattered components of light. The top view of the phase shifter is shown in FIG. 1B. This particular phase shifter is stepped laterally to change the phase of the unscattered component from one value to another value, however other configurations could be rotated about an axis or moved laterally in two axis to achieve a similar result. The number of phase shifting elements in the example system is three, but it does not need to be limited to three and can be arbitrarily large. The phase we care about is not the absolute phase. What we care about is the relative phase between the scattered and unscattered components. Therefore, the phase shifting element can be in the path of either the unscattered or scattered component. However, a phase shifting element in the path of the unscattered component is generally preferred because the etendue of the unscattered component is usually much smaller than that of scattered component making it much easier to fabricate. In FIG. 1A, a phase shifting element 174 is in the path of the unscattered component. The phase of the unscattered component is changed when the phase shifting element is changed to another phase shifting element. The unscattered component 120 can also be attenuated to improve the contrast of the raw image by adding a partially absorbing or reflecting surface in the path of unscattered component.

There are a variety of ways of making a phase shifter. One simple way of making a phase shifter is by applying thin film coatings or etching shallow wells at multiple places on a glass plate such as that shown in FIGS. 1A and 1B. In the accompanying figures, the thickness (or depth) and lateral extent of the thin films (or wells) are highly exaggerated in order to render them visible. The actual film thicknesses and well depths are only an order of a wavelength. Their lateral extent is usually less than 100 µm. Therefore, the thin films and wells form tiny islands or pits on a transparent glass plate as shown in FIG. 1B. Thin films and wells can be formed into other shapes such as a ring shape as in conventional phase contrast microscope. This kind of shape allows us to use an extended light source such an arc lamp, halogen lamp, etc. However, this configuration has the disadvantage of introducing phase changes to some portion of the scattered component of the collected light resulting in degradation in the image quality. Thus, the use of this kind of extended shape of phase shifter is discouraged. A laser beam with a single spatial mode along with phase shifting elements made as small as allowed by diffraction theory is the preferred choice herein. Shallow wells can be created by etching away a small amount of material from the glass substrate. Conceptually, a shallow well can be considered as a thin film with negative thickness and similarly a thin film can be considered as a shallow well with negative depth. Therefore, the meanings of "thin film" and "shallow well" are broadened to include each other and the two words are used in this broader sense herein.

Thin film type phase shifters have several drawbacks. The most severe drawback is that they cannot shift the phase in a continuous fashion. Only discrete phase shifts are allowed. This discreteness in phase shifting can compromise the performance of the system for some applications. Another drawback is that phase change requires a mechanical movement of the phase shifter plate to shift the phase. Mechanical movement is usually slower than other kinds of controls such as electro-optical control and hence can affect the speed of the system significantly. However, the thin film type phase shifter has important advantages too. First, it is not sensitive to the polarization of the input light. That is, it allows any polarization to pass through without any significant change in polarization. This is important because it allows us to change the polarization of the illumination light freely with no change to the phase shifter. The polarization of the illumination light needs to be changed freely in many applications for important purposes such as to improve the image quality, to examine the polarization sensitivity of the sample, etc.

Another important advantage of a thin film type phase shifter is that it does not require any wiring in the light path. Obscuration cased by wiring traversing the light path, which is usually unavoidable in the case of an electrically-controlled phase shifter, can result in degradation in image quality or system performance. The degradation can be too large to be tolerated for applications, which require a faithful image quality.

Thus, eliminating the need for wiring can be an important advantage for a thin film type phase shifter for some applications. Another advantage of a thin film type phase shifter is that it requires minimal design changes in most conventional microscope lenses. The thin film type phase shifter can often be made small enough to fit into a conventional microscope lens train without significant modifications. Usually it can be retro-fitted into a conventional phase-contrast microscope system without changing the lens prescription. Only the fixed phase plate of a phase contrast microscope needs to be replaced with a movable phase shifter plate along with an appropriate modification of the lens mount and barrel to allow the mechanical movement.

In order to determine the complex amplitude of an image-forming field, the amount of phase change each phase shifting element introduces to the passing beam must be known accurately. There are several different methods that can determine the amount of phase shift each phase shifting element introduces to the passing beam. They include physical measurement of film height, ellipsometric measurement of the film characteristics, etc. However, the most straightforward way of determining the phase shift is to use a conventional phase-shifting interferometer such as Twyman-Green interferometer. This kind of measurement can achieve an accuracy of a few degrees without difficulty and much higher accuracy with more careful handling of the instrument.

Optimal performance of the interferometric imaging system requires accurate lateral alignment of the phase shifting element to the unscattered component at the pupil plane. This kind of alignment can be done in several different ways such as lateral scanning of the phase shifter plate while observing the intensity distribution at the image plane. The unscattered component at the image plane will be most uniform when the center of the unscattered component is aligned with the center of the phase shifting element. Of course, the illumination ray can be adjusted rather than the phase shifter plate. This is because absolute positions of the unscattered component and the phase shifting element at the pupil plane are not important but only their relative positions are important. This alignment method has an advantage of not requiring extra hardware.

However, this alignment method has a drawback that sometimes the phase shifting element can miss the unscattered component completely and a time-consuming spiral search of the unscattered component may be required. This kind of drawback can be avoided if we image the pupil plane on an image sensor using a pupil-relay lens. This technique requires extra hardware. However, it allows an accurate visual alignment of the phase shifter to the unscattered component. The pupil-relay lens system does not need to be diffraction-limited or highly corrected. Also, the existing primary image sensor can be used for this purpose. Therefore, this alignment method is generally preferred in most applications.

In some applications such as searching for a special feature, defect detection, etc., it is desirable to filter out the unwanted parts of the image-forming light. This can usually be done most effectively substantially at the pupil plane. The complex amplitude distribution of the image-forming field at the pupil plane is the Fourier-transform of the complex amplitude distribution of the image-forming field at the object plane. Therefore, this kind of light filtering is called Fourier filtering. A Fourier filter cannot only keep the unwanted light away from the image sensor but can also make the intensity of the image more uniform across the field. More uniform image intensity allows for better use of the dynamic range of the image sensor for the noiseless amplification of the weak image-forming field.

Figure 1C:
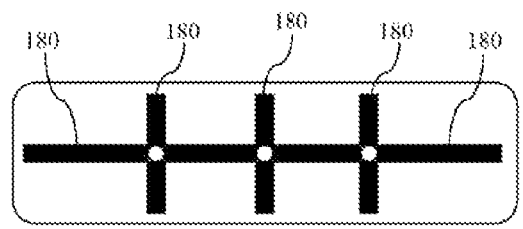
FIG. 1C shows a phase shifter with Fourier filters.

A Fourier filter can be made of a variety of different materials such as reflecting film, opaque metal strips, etc. A Fourier filter can be installed in the pupil plane separately from the phase-shifter plate. However, a Fourier filter can also be attached to the phase-shifter plate as shown in FIG. 1C. In this case the Fourier filter consists of the opaque strips 180 in FIG. 1C. The attached Fourier filter is less flexible in changing its shape. However, it has an important advantage of mechanical simplicity. The Fourier filter 180 shown in FIG. 1C will filter out most of the diffracted light from Manhattan patterns but will not be effective in filtering out the diffracted light from other kinds of patterns. Therefore, the shape of the Fourier filter needs to be changed according to the diffraction patterns to be filtered out. For example, additional metal strips can be introduced in the pupil plane if a part of the patterns to be filtered are not Manhattan patterns.

A Fourier filter does not always need to be made with opaque or reflective materials. Such a filter is called a binary filter because either it transmits or it doesn't. It is also possible to add a phase component to the filter by adding semi-transparent materials or even completely transparent materials such as dielectric films. These kinds of phase and amplitude Fourier filters can be very effective in increasing the visibility of some patterns or features and decreasing the visibility of other patterns. For some applications such as the observation of complicated patterns or features, a very sophisticated phase and amplitude Fourier filter can be used in order to increase the image quality or visibility.

It has been found that too much Fourier filtering can be detrimental because the Fourier filter can block the useful part of image-forming field as well as the harmful part. The blocking of the useful part of the image-forming field can impact the final image quality in two ways: it not only reduces the total amount of image-forming light collected but also makes the image a little fuzzier through diffraction. There is usually an optimum amount of Fourier filtering that depends on the application A Fourier filter made of an absorbing material like metal can become hot during operation, especially in industrial applications where powerful light sources are usually used. A hot Fourier filter not only can cause mechanical problems because of differential expansion and warping but also optical problems because it can heat the surrounding air and optical elements unevenly, which in turn can distort the wavefront of the image-forming field. However, this kind of heat problem can be resolved or mitigated by flowing a gas with high thermal diffusivity like helium around the Fourier filter. Helium gas is especially suitable because its refractive index is very low and therefore doesn't change much with density or temperature.

Figure 2:
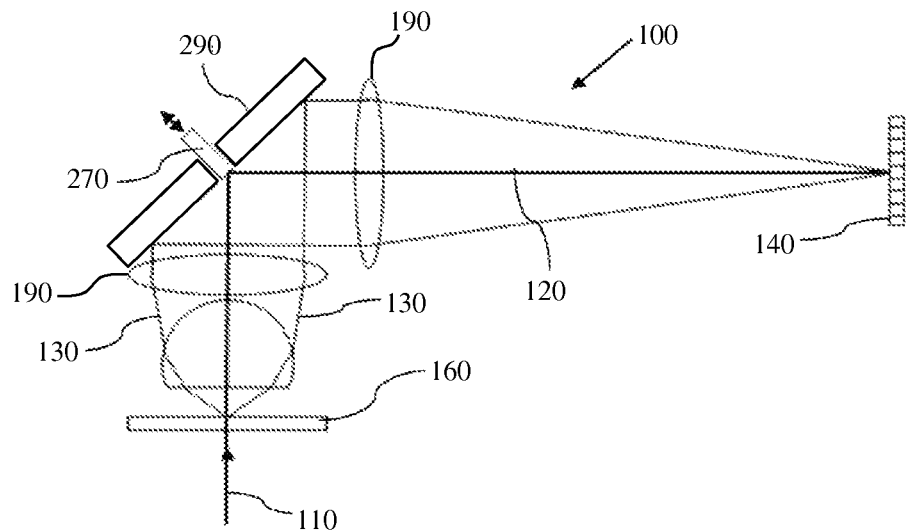
FIG. 2 shows an example of a high-resolution common-path interferometric imaging system with a reflective phase shifter, according to some embodiments.

The phase shifter does not need to be transmissive. A reflective phase shifter can be made easily using a small movable mirror. This kind of phase shifter is depicted in FIG. 2. A fixed mirror 290 with a hole in the center is placed in the vicinity of the pupil. A small movable mirror 270 is introduced through the hole. Phase shift can be achieved by moving the small mirror 270 in the normal direction to the fixed mirror surface. This kind of reflective phase shifter is useful when it is hard to find transmissive materials as in the case when vacuum ultraviolet light, extreme ultraviolet light, etc. needs to be used as the light source.

Another possibility for fabricating a reflective phase filter is to employ a large reflective plate containing a variety of smaller reflective areas that either protrude or are recessed from the plate surface and which may be positioned to shift the phase of the un-scattered beam with respect to the scattered beam.

Other kinds of phase shifters such as an electrically-controlled phase shifter can be employed. Good examples of electrically-controlled phase shifter are electro-optic and liquid crystal phase shifters. Many books and articles describe how to build electrically-controlled phase shifters. For example, the construction of an electro-optic phase shifter is well-described in Handbook of Optics Volume II, Second Edition, McGraw-Hill, Inc, 1995, pp 13.15-13.18. The construction of a liquid crystal phase shifter is well-described in H. Kadono, M. Ogusu, S. Toyooka "Phase shifting common path interferometer using a liquid-crystal phase modulator" Optics Communications 110 (1994) 391-400. Electrically-controlled phase shifters are fast and do not require any moving parts. However, they are usually polarization sensitive and work as a pure phase shifter only for two specific polarization states called eigen polarizations. Refer to Kenneth F. Hulme "Oblique-Cut Longitudinal Electro-optic Modulators", IEEE Journal of Quantum Electronics, Vol. QE-7, No. 6, June 1971 for the discussion of polarization sensitivity of electro-optic modulators.

Many other kinds of phase shifters are also available. The construction of other types of phase shifters is described in WO 2009/149103 A1 "Interferometric Defect Detection and Classification". Some phase-shifters, especially electro-optical ones, are fast-acting. Some of the other phase-shifters, especially the ones requiring mechanical motion, are relatively slow-acting. A fast-acting phase shifter is needed if multiple pictures need to be taken in a short period of time with a different phase value for each picture. However, a slow-acting phase shifter will be fine if the sample does not change with time.

Varying the phase of a phase shifter during the period of image-taking is not desirable. However, if the phase shifter is a slow-acting type, it may be necessary in some applications to allow the phase value to vary continuously while taking an image of the sample. In this case, the interference term is convolved with a window function, which represents the period of phase variation during the image-taking. Consequently, all the interference terms in the equations shown in the Theory section must be multiplied by the convolution factor which must be equal to or smaller than 1. For example, if the phase varied by $\Delta\theta$ in a continuous fashion during the image-taking period, then:

$$I = \frac{1}{\Delta\theta} \int_{\theta_n - \frac{\Delta\theta}{2}}^{\theta_n + \frac{\Delta\theta}{2}} [|b|^2 + |g|^2 + D + 2|b||a|\cos(\varphi_a + \theta)] \, d\theta \quad (65)$$

$$= |b|^2 + |g|^2 + D + \operatorname{sinc}\left(\frac{\Delta\theta}{2}\right) \cdot 2|b||a|\cos(\varphi_a + \theta_n) \quad (66)$$

Thus, in this case, the convolution factor is $$\mathrm{sinc}\left(\frac{\Delta\theta}{2}\right) \equiv \frac{\sin\left(\frac{\Delta\theta}{2}\right)}{\frac{\Delta\theta}{2}}.$$

A different type of window function will produce a different type of convolution factor. In any case, as long as the phase-varying period is short enough to prevent the convolution factor from becoming significantly smaller than 1, the continuous varying of the phase during image-taking period can be tolerated.

The phase shifter is preferably placed substantially at the pupil, i.e., at or close to the pupil or the pupil conjugate of the optical imaging system, in order to spatially separate the unscattered component from the scattered component in a clean fashion and also to achieve uniform performance over the whole imaging field. The primary pupil conjugate is the aperture stop of the optical imaging system. The phase shifter 170 is placed at or close to the aperture stop plane of the imaging system shown in FIG. 1A. Placing the phase shifter at or close to the aperture stop plane of the optical imaging system is most ideal because it does not require additional optical parts that are not only bulky and costly but also can reduce image quality and energy efficiency. If a laser is used as the light source and the sample is illuminated coherently, the size of the unscattered component at the pupil conjugate plane becomes very tiny, usually smaller than 100 μm, and consequently, the phase shifting element can be made tiny so as not to take much space or interfere with other parts. Thus, the new disclosure allows us to place the phase shifter directly at or close to the aperture stop plane of the optical imaging system, even if the pupil area is narrow and crowded with other parts. This is one of the practical advantages of the new disclosure. If the aperture stop area is absolutely too small or too crowded to allow the presence of a phase shifter, then the aperture stop plane can be relayed to a less crowed area by adding a high quality pupil relay system. However, this should be the last resort because it not only brings in a lot of undesirable side effects, but also, in many cases, especially in the case of high etendue DUV systems, it is extremely difficult and costly to design and build a decent pupil relay system.

Additional system components are shown in the example embodiment of system 100 of FIG. 1A. They include a controller 142, such as a computer or like machine, that is adapted (e.g., via instructions such as software embodied in a computer-readable or machine-readable medium) to control the operation of the various components of the system. Controller 142 is configured to control the operation of system 100 and includes a processing unit ("signal processor") 152 electrically connected to sensor system 140 and adapted to receive and process the digitized raw electronic signal therefrom and form processed image signals, as described in greater detail below. In an example embodiment, signal processor 152 is configured to process the raw image signal and reconstruct the sample image. As used herein, the term "electronic or electrical signal" includes both analog and digital representations of physical quantities and other information.

Signal processor 152 is or includes any processor or device capable of executing a series of software instructions and includes, without limitation, a general or special-purpose microprocessor, finite state machine, controller, computer, central-processing unit (CPU), graphical-processing unit (GPU), massively parallel processor, field-programmable gate array (FPGA), or digital signal processor.

Memory unit ("memory") 154 is operably coupled to signal processor 152. As used herein, the term "memory" refers to any processor-readable medium, including but not limited to RAM, ROM, EPROM, PROM, EEPROM, flash memory, disk, floppy disk, hard disk, CD-ROM, DVD, or the like, on which may be stored a series of instructions executable by signal processor 152 or data to be used by or generated by signal processor 152. In an example embodiment, controller 142 includes a port or drive 156 adapted to accommodate a removable processor-readable medium 158, such as CD-ROM, DVD, memory stick or like storage medium.

The interferometric imaging method described herein may be implemented in various embodiments in a machine-readable medium (e.g., memory 154) comprising machine readable instructions (e.g., computer programs and/or software modules) for causing controller 142 to perform the methods and the controlling operations for operating system 100. In an example embodiment, the computer programs run on signal processor 152 out of memory 154, and may be transferred to main memory from permanent storage via disk drive or port 156 when stored on removable media 158, or via a network connection or modem connection when stored outside of controller 142, or via other types of computer or machine-readable media from which it can be read and utilized.

The computer programs and/or software modules may comprise multiple modules or objects to perform the various methods of the present disclosure, and control the operation and function of the various components in system 100. The type of computer programming languages used for the code may vary between procedural code-type languages to object-oriented languages. The files or objects need not have a one to one correspondence to the modules or method steps described depending on the desires of the programmer. Further, the method and apparatus may comprise combinations of software, hardware and firmware. Firmware can be downloaded into signal processor 152 for implementing the various example embodiments of the disclosure.

Controller 142 also optionally includes a display unit 146 that can be used to display information using a wide variety of alphanumeric and graphical representations. For example, display unit 146 is useful for displaying raw signals, processed signals, reconstructed images, or physical properties of the sample. Controller 142 also optionally includes a data-entry device 148, such as a keyboard, that allows an operator of system 100 to input information into controller 142 to control the operation of system 100.

In an example embodiment, controller 142 is operably connected to or is part of sensor system 140. In another example embodiment, controller 142 is operably connected to a sample positioning system 150 for positioning the sample, and to an actuator 144 for adjusting the phase using phase shifter and attenuator 122. Controller 142 is shown only in system 100 of FIG. 1A for ease of illustration, however it can be included in all example embodiments described herein.

Figure 3:
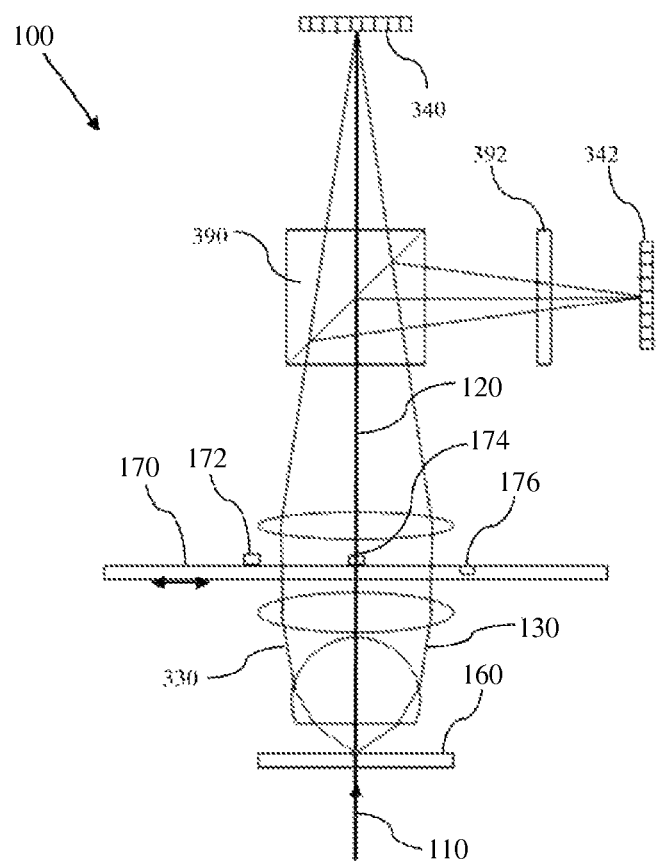
FIG. 3 shows an example of a high-resolution common-path interferometric imaging system combined with a conventional imaging system, according to some embodiments.

Another system configuration is shown in FIG. 3. The imaging path is split into two paths using a wavelength sensitive beam-splitter 390, one for interferometric imaging at the image sensor 340 and the other for conventional imaging at the image sensor 342. The conventional imaging path can be used, for example, for the imaging of fluorescent light that originates from the fluorescing sample. A filter 392 in the conventional imaging path removes the illumination wavelength leaving only the fluorescent wavelength on detector 342. This configuration allows simultaneous imaging of different wavelengths and can be very useful for bio-medical applications.

Figure 4:
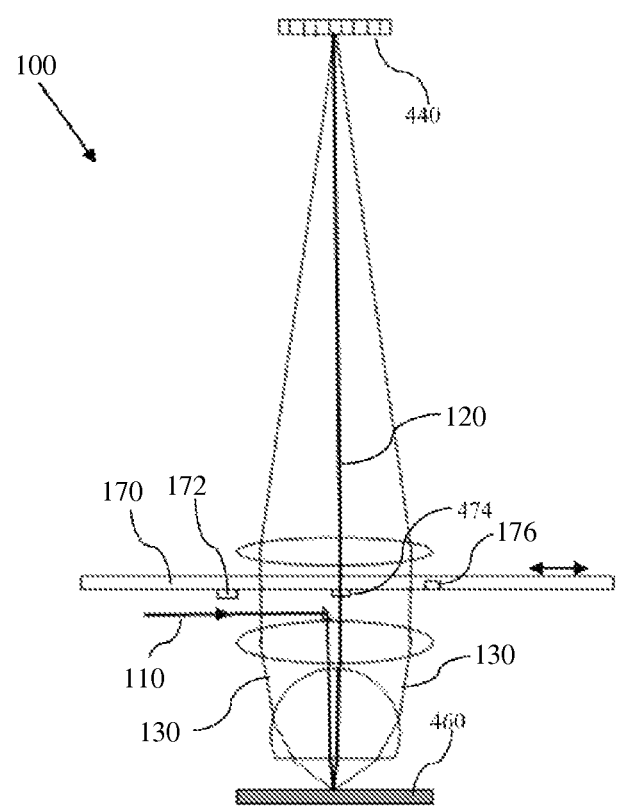
FIG. 4 shows an example of a high-resolution common-path interferometric imaging system employed in reflection mode, according to some embodiments.

Another system configuration is shown in FIG. 4. The system is configured for the imaging of a reflective sample 460. A part of the illumination light is reflected unscattered and passes through a phase shifting element 474. Another part of the illumination light 430 is scattered or diffracted by the sample and collected by the imaging system 400. The working principle of the reflective configuration is identical in principle to that of the transmissive case.

Figure 5:
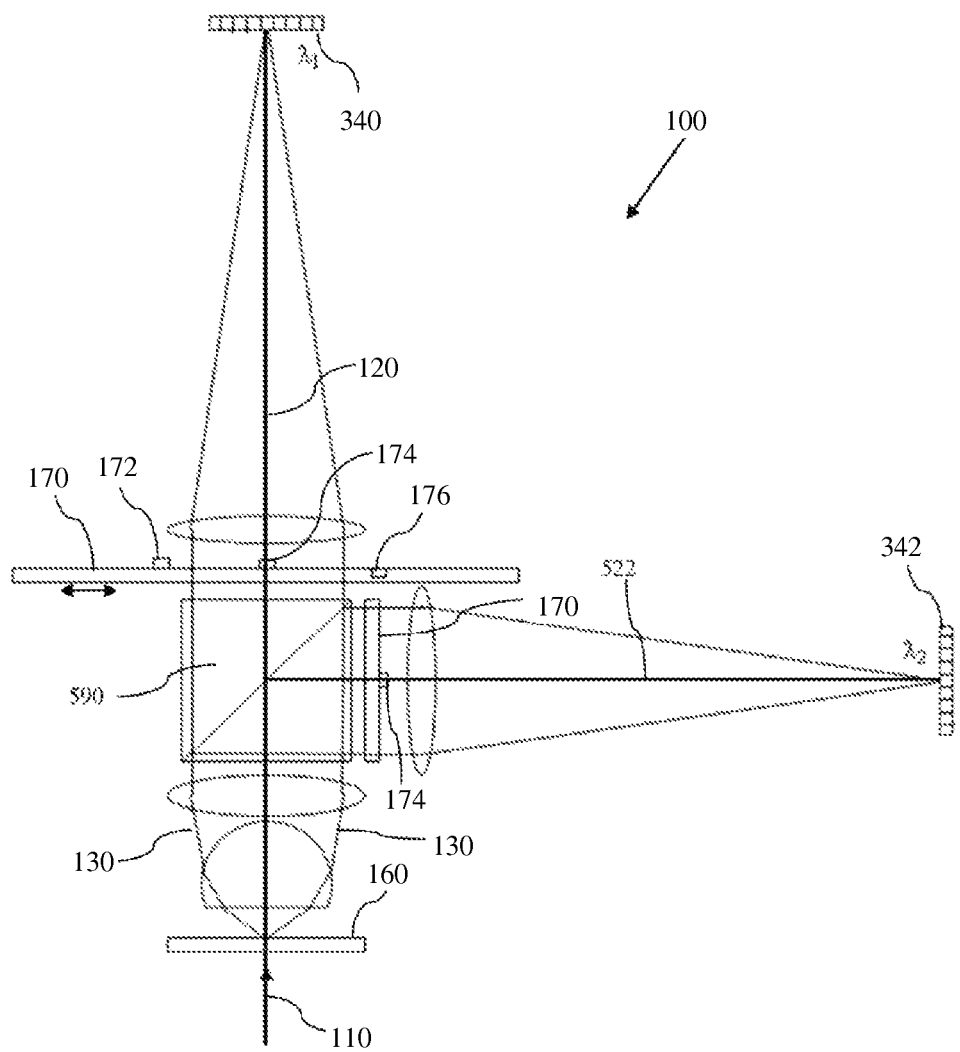
FIG. 5 shows an example of a high-resolution common-path interferometric imaging system for two wavelengths, according to some embodiments.

Another system configuration is shown in FIG. 5. This system is configured for the use of two wavelengths, $\lambda_1$ and $\lambda_2$. The two wavelengths share the front-end of the imaging system but are split into separate paths using a wavelength sensitive beam-splitter 590 in the rear end of the imaging system. Each wavelength can have its own phase shifter 174 as shown in FIG. 5. However a common phase shifter 174 is also possible provided that the different phase shift introduced to each different wavelength is taken into account in the data reduction. More wavelengths can be added by using additional wavelength splitters. An imaging system capable of handling multiple wavelengths is more complicated and expensive. However, it can expand the scope of applications of the interferometric imaging technology.

Figure 6:
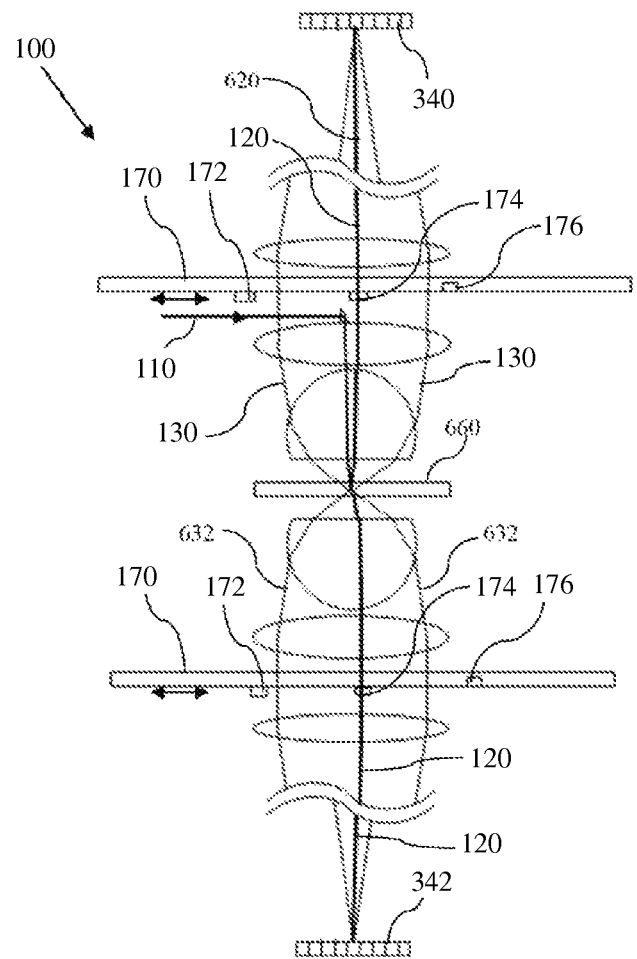
FIG. 6 shows an example of a high-resolution common-path interferometric imaging system employed in dual mode, according to some embodiments.

Another system configuration is shown in FIG. 6. This system is a dual mode system. That is, it collects both transmitted light 632 and reflected light 130 to examine the sample in a more thorough fashion.

A variety of other possible system configurations are described in WO 2009/149103 A1 "Interferometric Defect Detection and Classification". Those configurations include several configurations employing illumination light with a high angle of incidence, and several configurations with an extended light source, and a configuration with multiple wavelengths, etc.

III. Operational Modes

The systems described herein can be operated in many different ways. Further details on some of the different system operational modes are set forth below.

1. Complex-Amplitude Mode.

Objects or samples can alter not only the amplitude but also the phase of the scattered light. Different materials affect both the amplitude and the phase of the scattered light differently. Therefore, if both the amplitude and phase of the scattered light are measured, not only can objects be imaged more clearly but also more information about the objects can be obtained. The complex-amplitude mode is based on the determination of both the amplitude and the phase of the image-forming field. Aberrations and distortions in the image can be removed in the complex-amplitude mode as explained in the Theory section. The methods and needed equations for the determination of both amplitude and phase of the image are presented in the Theory section.

Figure 7A:
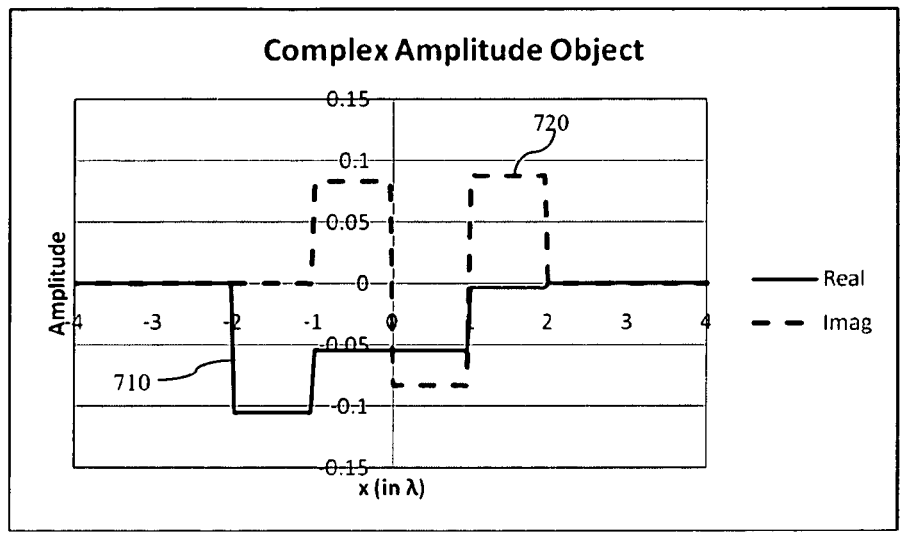
FIG. 7A shows the complex amplitude of a one dimensional object that is used for imaging simulations herein.
Figure 7B:
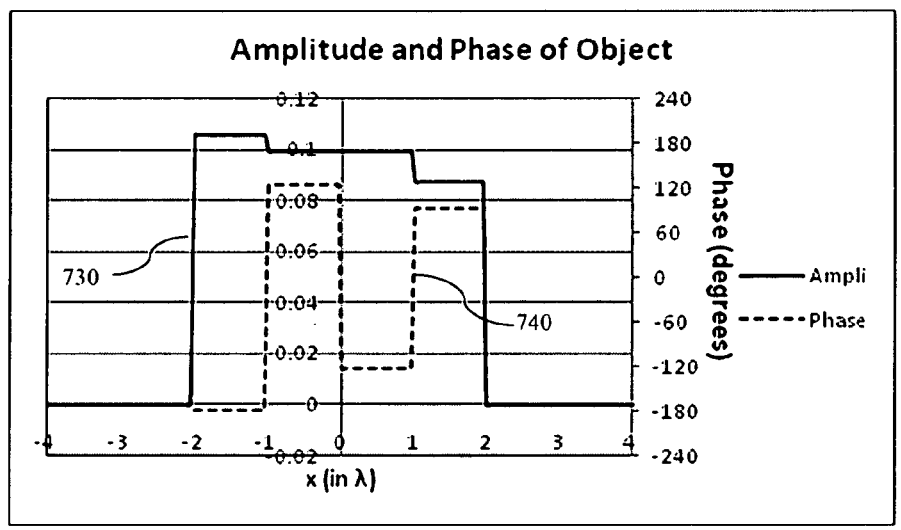
FIG. 7B shows the amplitude and phase of the same one dimensional object shown in FIG. 7A.
Figure 8:
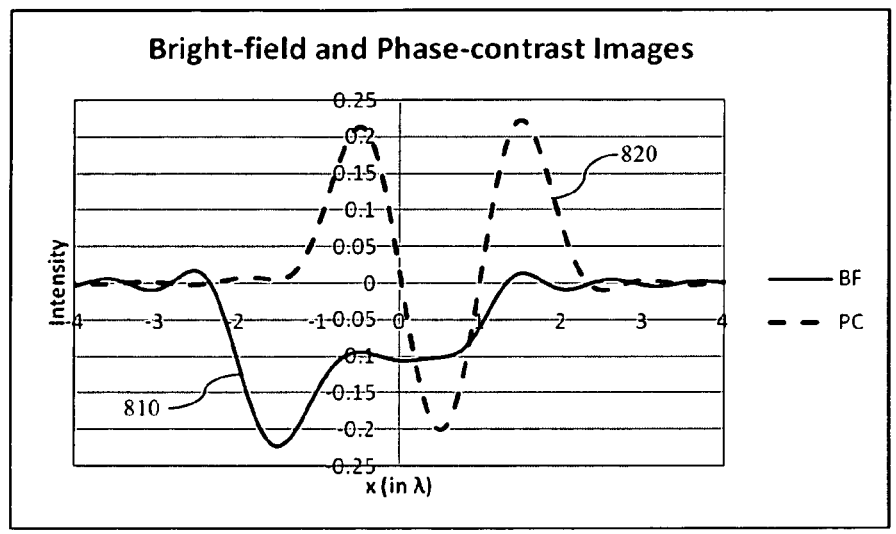
FIG. 8 shows the simulated images from a conventional bright-field and phase-contrast imaging techniques.

An example of the complex-amplitude mode of operation is illustrated in FIG. 7A, which shows the real part, 710, and the imaginary part, 720, of the complex amplitude of a weakly scattering one-dimensional object with illumination normal to the sample surface. The complex amplitude of the object is defined as the complex amplitude of the scattered component at the object plane before leaving the object. The complex amplitude of the object can have a lot of high spatial frequency components that cannot propagate through the free space. These non-propagating components are called non-radiative or evanescent components. These components cannot be collected by the imaging system because they do not leave the object. FIG. 7B is the representation of the same complex amplitude of the object in polar coordinates in the complex plane. The real and imaginary parts of the complex amplitude, 710 and 720 respectively, shown in FIG. 7A are converted to amplitude 730 and phase 740 in FIG. 7B. FIG. 8 shows the images 810 and 820 from a conventional optical system whose numerical aperture (NA) is 0.9. The images are not as sharp as the object because all imaging systems act as a low-pass filter cutting off the spatial frequency components of coherently illuminated objects higher than $$\frac{NA}{\lambda}.$$

Figure 9:
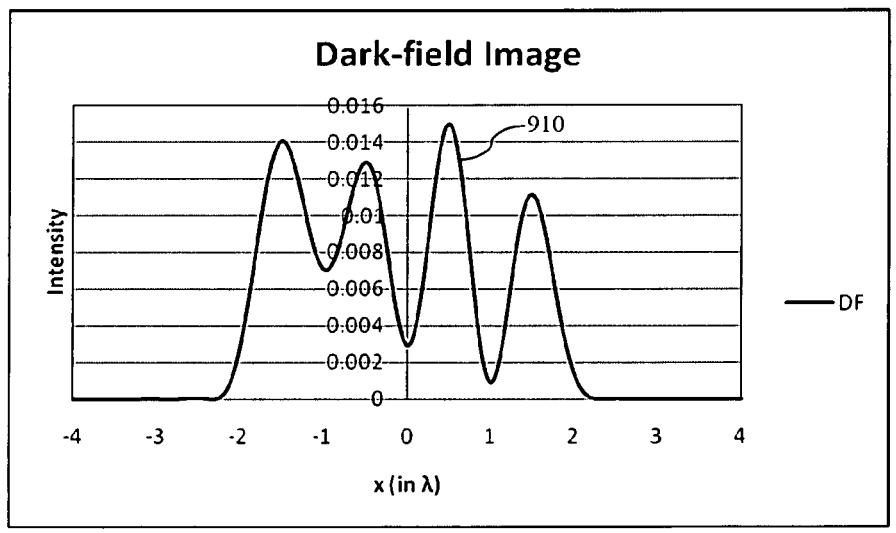
FIG. 9 shows the simulated image from a conventional dark-field imaging technique.

A comparison of FIG. 8 with FIG. 7A shows the shortcoming of conventional imaging systems. This tells us that the image 810 from a conventional bright-field system generally depicts only the real part of the image-forming field, and the image 820 from a conventional phase-contrast system depicts only the imaginary part of the image-forming field. Note that the two conventional imaging systems depict the real and imaginary parts of the image-forming field quite faithfully in this example because the scattered component is assumed to be weak compared with the unscattered component. If the scattered component is strong, the two conventional systems will not be able to depict the real and imaginary parts of the image-forming field faithfully. FIG. 9 shows the image 910 from conventional dark-field system. A comparison of FIG. 9 with FIG. 7B shows that the image from a conventional dark-field system depicts only the intensity of the image-forming field ignoring the phase of the image-forming field completely. Thus, conventional imaging systems can show only a part of the information carried by an image-forming field. This is a critical drawback of conventional imaging systems that limits their application.

Figure 10A:
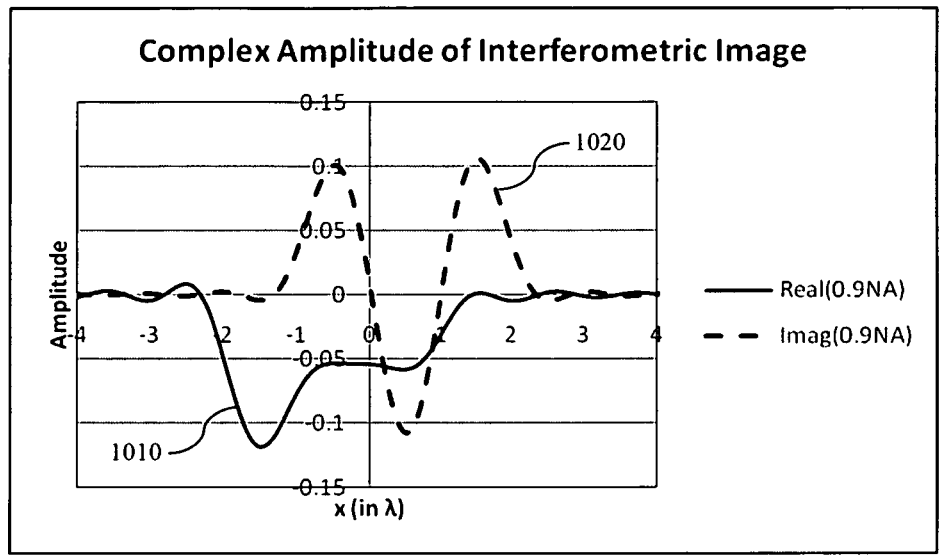
FIG. 10A shows the complex amplitude of an image-forming field in Cartesian coordinates obtained with the interferometric imaging technique disclosed herein.
Figure 10B:
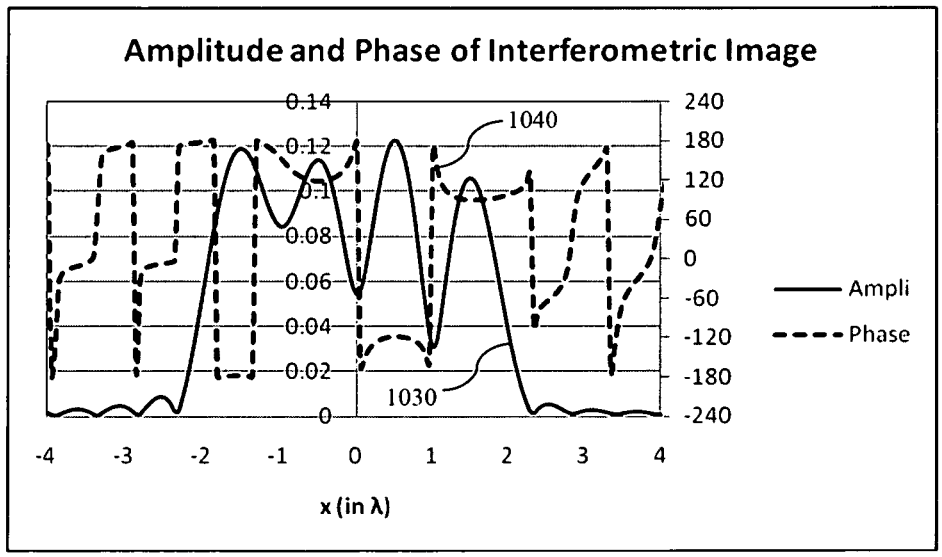
FIG. 10B shows the amplitude and phase of the same image-forming field shown in FIG. 10A in polar coordinates.
Figure 10C:
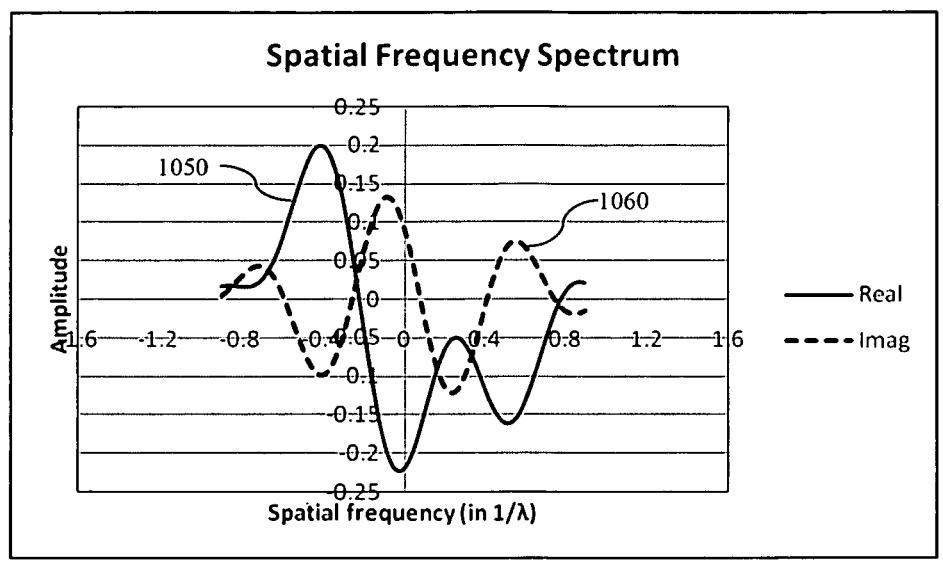
FIG. 10C shows the complex amplitude of the image-forming field at the pupil plane, which is a Fourier-transform of the complex amplitude of the same field at the image plane.

FIG. 10A shows the image from the interferometric imaging system disclosed herein. This image was obtained by processing the multiple images taken with different phase settings as described in the Theory section. The interferometric image shows the complex amplitude, i.e. both the real and imaginary parts 1010 and 1020 respectively, of the image-forming field. The complex amplitude shown by the interferometric imaging system is true and accurate no matter what the strength of image-forming field is. That is, even if the sample scatters the illuminating light strongly, the interferometric image shows the complex amplitude of the image-forming field truly and accurately. This is one of the important properties of interferometric images that allows quantitative analysis and evaluation of the image-forming field and some physical properties of the sample. FIG. 10B is the representation of the complex amplitude of the image-forming field in a polar coordinate system. It shows the true amplitude 1030 and phase 1040 of the image-forming field accurately. Thus, an interferometric imaging system picks up all the information contained in an image-forming field accurately and faithfully. This is a major departure from existing imaging technologies and can expand the scope of optical imaging technology beyond the current limits. FIG. 10C shows the spatial frequency spectrum of the same image shown in FIG. 10A. The real and imaginary parts of the spatial frequency spectrum, 1050 and 1060 respectively, are exactly the complex amplitude distribution of image-forming light field at the pupil plane. It is included herein for comparison with other spatial frequencies in a later section on the Super-resolution mode of operation.

If the dynamic range of the image sensor is large, the noiseless amplification of the image-forming field by the strong unscattered component can be used effectively for clean amplification of the weak image-forming field. This technique allows the production of a good quality image of an object that scatters only a tiny amount of light. Currently, scientific grade CCD and TDI CCD detectors have a very large dynamic range. Therefore, the technique of noiseless amplification of a weak image-forming field using the strong unscattered component is not just a theory, but a very practical means to improve image quality significantly.

Note that a strong unscattered component for a large noiseless amplification implies a very low contrast in the raw image. Thus, the new disclosure can cope with a low-contrast raw image by amplifying the weak image-forming field as much as possible. This is quite the opposite of conventional imaging techniques, which normally try to achieve the highest contrast in the raw image by minimizing the unscattered component.

2. Tomographic Mode.

If the sample is tiltable or rotatable around an intersection point between the sample and the optical axis of the imaging system, even the 3-dimensional complex refractive index distribution inside the sample can be obtained by processing a large number of complex amplitude images of the sample taken at a multitude of different tilt angles using the well-known tomographic image processing technique which is well described in many books such as Max Born and Emil Wolf, "Principles of Optics, $7^{th}$ edition", Cambridge University Press, 1999, pp 217-227, and Ronald N. Bracewell, "The Fourier Transform and Its Applications, Third Edition", McGraw Hill, 2000, pp 356-358. This tomographic technique can provide potentially high volumetric or 3-dimensional resolution.

However, there are several difficulties in practice. First, the thickness of the sample must be smaller than the depth of focus of the imaging system. Otherwise, the image can be blurred too much. If the sample is thicker than the depth of focus of the imaging system, either the sample must be made thinner or the numerical aperture of the imaging system must be reduced to increase its depth of focus. Second, the sample should be made of weak scatterers. That is, the variation of the complex refractive index inside the sample should be small. Otherwise, diffraction effects cannot be ignored and consequently the conventional tomographic technique cannot be used for image processing. Third, there can be a conflict between the field of view and the volumetric resolution. That is, high volumetric resolution requires a large number of tilts or rotations of the sample, but a large tilt or rotation of the sample puts most parts of the sample out of focus resulting in a small usable field of view. Fourth, the sample may need to be placed inside an index-matched oil tank. Otherwise, the beam may walk off too much when the sample plate is tilted or rotated. Even with all these drawbacks, the tomographic mode can still be useful for high-resolution, volumetric or 3-dimensional imaging of small samples.

There are other optical volumetric techniques such as confocal microscopy and optical coherence tomography. However, they extract only intensity or amplitude information from the measurement. It is therefore next to impossible for them to extract phase information, while the tomographic mode described herein can provide both amplitude and phase information.

3. Super-resolution Mode

One of the important advantages of the interferometric imaging technique disclosed herein is that the reconstructed image can have a much higher spatial resolution than the image obtained from conventional imaging techniques through the use of so called pupil synthesis. Higher spatial resolution means a wider spatial frequency range. Therefore, pupil synthesis herein means a virtual increase of the pupil diameter or numerical aperture through the processing of multiple images taken with illumination rays tilted at various angles. Note that "pupil synthesis" will also be called "aperture synthesis" or "numerical aperture synthesis" herein. Those words will also be used either with or without the adjective "extended" in the front herein.

Figure 11A:
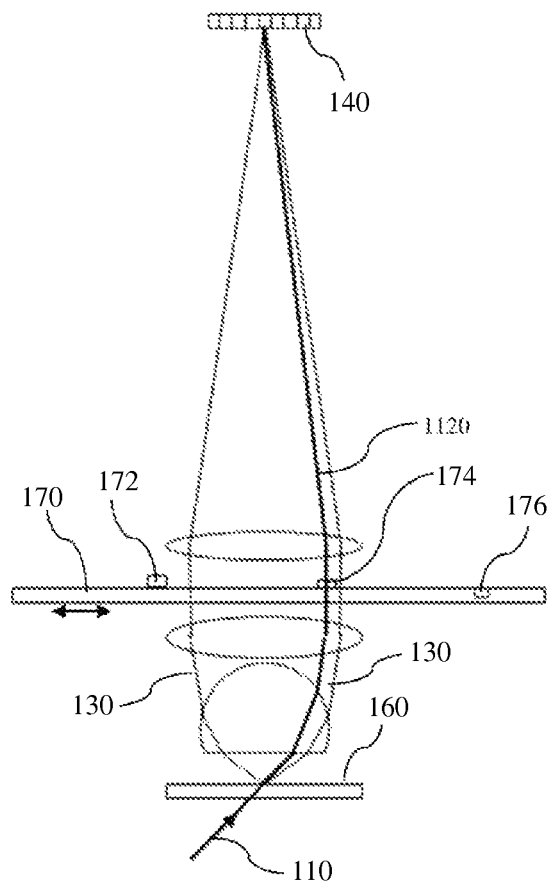
FIG. 11A shows an example of a high-resolution common-path interferometric imaging system with a tilted or oblique illumination ray for the collection of higher spatial frequency components, according to some embodiments.
Figure 11B:
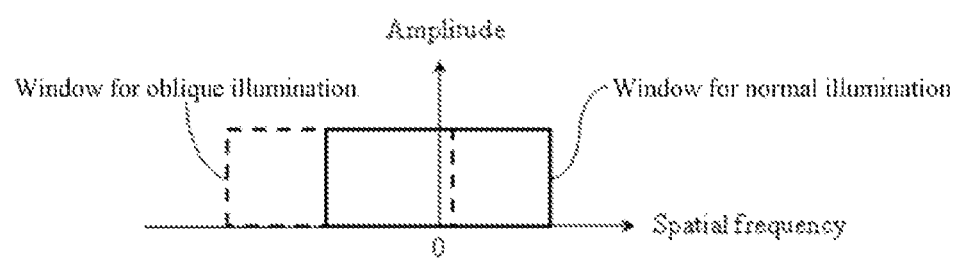
FIG. 11B shows that employing oblique or tilted illumination is equivalent in effect to shifting the collection window in the pupil plane.
Figure 12A:
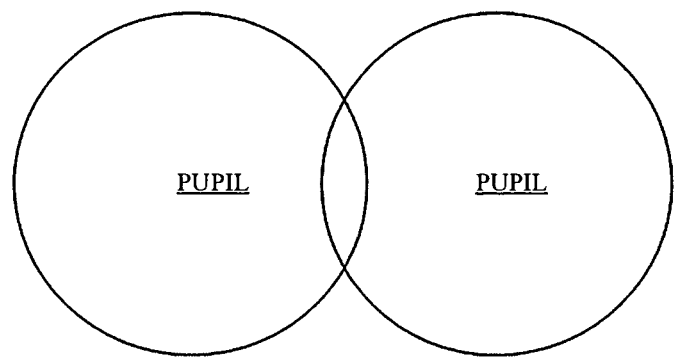
FIG. 12A shows an example of the synthesis of an extended pupil using the results from two differently tilted illumination rays.
Figure 12B:
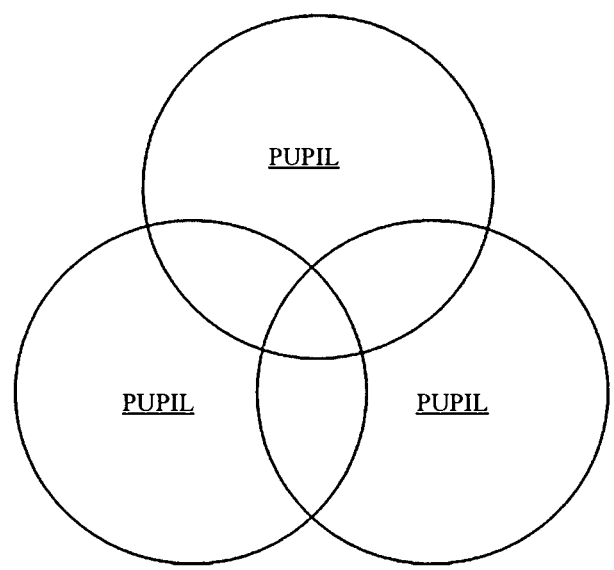
FIG. 12B shows an example of the synthesis of an extended pupil using three differently tilted illumination rays.
Figure 12C:
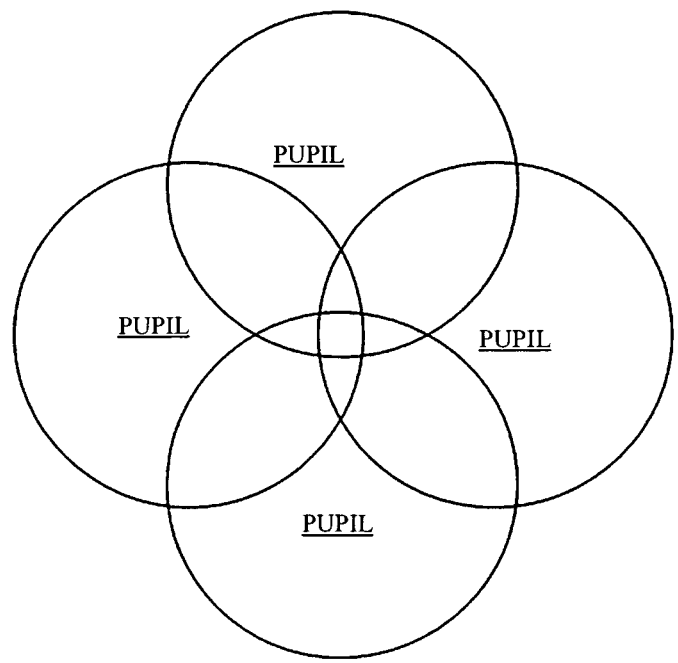
FIG. 12C shows an example of the synthesis of an extended pupil using four differently tilted illumination rays.
Figure 12D:
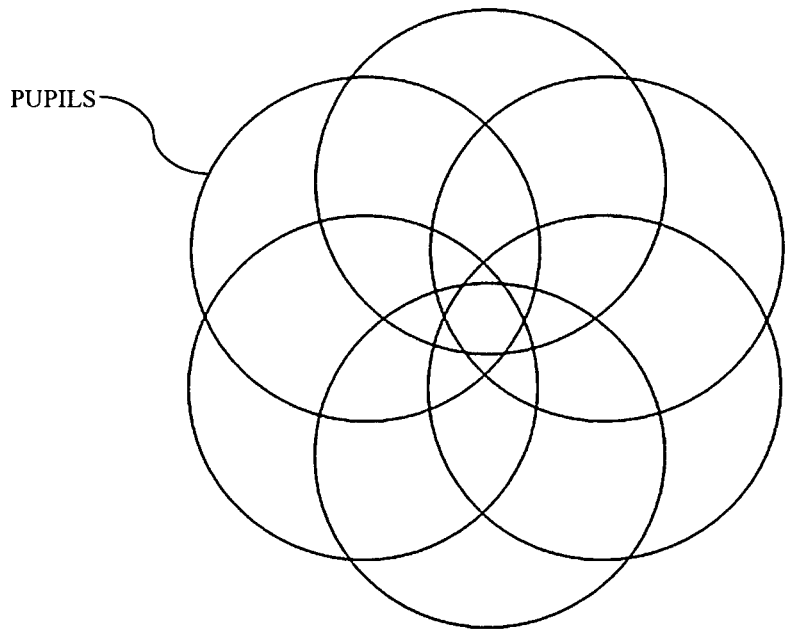
FIG. 12D shows an example of the synthesis of an extended pupil using six differently tilted illumination rays.

In order to understand how pupil synthesis works, let's see what happens if the illumination ray is tilted or oblique. If the illumination ray is tilted or oblique rather than normal to sample surface as shown in FIG. 11A, the position of the unscattered component 1120 at the pupil plane is laterally shifted from the center of the pupil. This is equivalent to a lateral shifting of the pupil without tilting the illumination ray, and therefore it shifts the spatial frequency spectrum obtained at the pupil as shown in FIG. 11B. The optical field at the pupil plane represents the spatial frequency spectrum of the sample i.e. the pupil is a window that determines the spatial frequency band that will be collected. Tilting the illumination ray is equivalent to shifting the collection window in the spatial frequency domain. This means that we can collect a different part of the spatial frequency band of the sample by tilting the illumination ray through different angles.

If we tilt the illumination ray and collect multiple images with different phase shifts and process the images using the equations presented in the Theory section, we can determine the complex amplitude of the image-forming field completely for that tilted illumination ray in the same way as it would have been determined with normal incidence illumination in the complex amplitude mode. This image-forming field is different from that with normal illumination because the collected part of the spatial frequency spectrum is shifted to include different spatial frequencies.

If we Fourier-transform the complex amplitude of the image-forming field, we can get its spatial frequency spectrum. The spatial frequency spectrum will show a shifted collection window in the spatial frequency domain that depends on the angle of the illumination ray. If we repeat the process for illumination rays tilted in many different directions, we can cover a spatial frequency spectrum spanning a much wider range.

Some parts of the spatial frequency spectra obtained with multiple tilted illumination rays will be overlapped with each other. The overlapping is important because it allows a coherent merging of the multiple spatial frequency spectra into a single, wider spatial-frequency spectrum. A coherent merge or combination of multiple spatial frequency spectra is achieved by adjusting their relative positions, relative angles, phase tilt angles, etc in order to minimize the spectral amplitude differences in the overlapping regions between different sub-spatial frequency spectra obtained with different illumination ray angles.

Two angles can describe the angular relationship between the incident radiation and the substrate. The incidence angle is measured in the plane containing the normal to the object plane and the vector describing the direction of the incoming illumination. The angle between the surface normal of the object plane and the vector is the incidence angle. Thus an incidence angle of 0° is normal incidence. The azimuth angle is the angle between a reference line on the sample and the line where the plane, containing the normal to the object plane and the vector describing the direction of the incoming illumination, intersects the object plane. Combining or averaging substrate data taken at different azimuth angles has to be done with the same orientation of the sample, i.e. the reference line on the sample must be pointed identically in all cases.

The spectral amplitude differences in the overlapped regions may not be made to vanish even with all the adjustments. There will usually exist small residual differences in the overlapped regions even with all the allowed adjustments due to the finite sample thickness, noise in the measurement, etc. In this case, average spectral amplitude values can be taken as the final values. Sometimes, some kind of smoothing of the spectral amplitude can be applied to the boundaries between different sub-spectral regions.

This spectra-merging technique is similar to the technique of combining sub-apertures into a larger single aperture in sub-aperture testing of a large mirror such as those used in astronomical telescopes. In this way, a much wider spatial frequency spectrum can be obtained by collecting multiple images with multiple tilted illumination rays and combining them coherently using an image processor. The wider spatial frequency spectrum obtained this way leads to much finer image resolution.

The pupil synthesis technique disclosed herein is very different from the incoherent superposition of different spatial frequency bands that is occurring in conventional microscopy or imaging systems with high sigma illumination. In conventional microscopy, spatial frequencies higher than $$\frac{NA}{\lambda}$$

can be obtained only with the loss of contrast at low spatial frequencies. On the other hand, the aperture synthesis technique disclosed herein allows us to obtain spatial frequencies higher than $$\frac{NA}{\lambda}$$

without losing contrast at lower spatial frequencies. This results in a much sharper image. For example, FIGS. 12A, 12B, 12C and 12D show extended pupils synthesized with two, three, four and six oblique illumination rays respectively.

Figure 13:
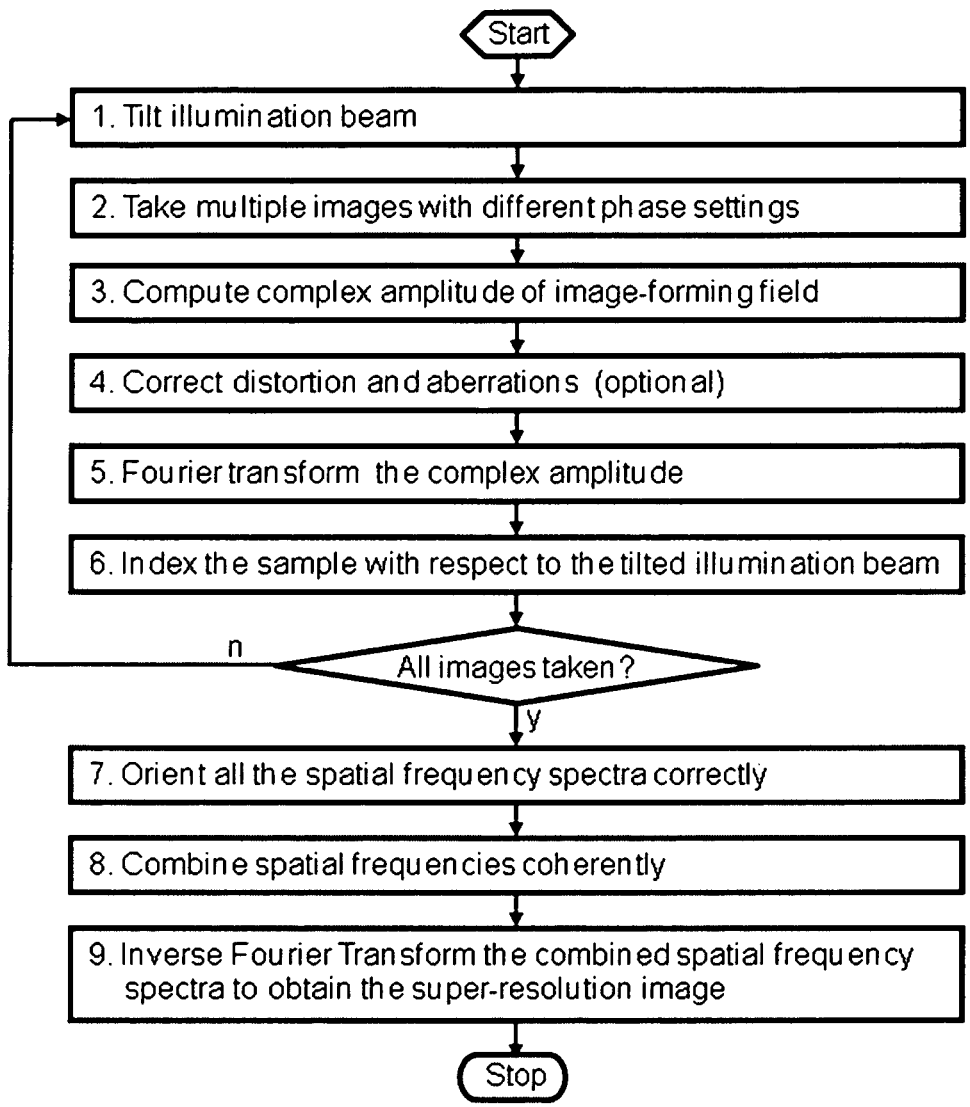
FIG. 13 shows the flow chart of the super-resolution mode of operation.

FIG. 13 shows the actual procedure for achieving a super-resolution image. First, the illumination ray is tilted by an appropriate amount. Then, multiple images with a different phase setting for each are collected to calculate the complex amplitude of the image-forming field using the equations presented in the Theory section. Then, if the amount of aberrations and/or the amount of distortion in the complex amplitude are more than is considered to be tolerable, they are corrected using the methods described in the Theory section. Next, the complex amplitude distribution is Fourier-transformed to get the complex amplitude distribution of the image-forming field at the pupil plane. The computed complex amplitude distribution at the pupil plane is indexed with respect to the tilted illumination ray and then stored in a memory device for coherent pupil synthesis at later step. Note that the complex amplitude distribution at the pupil plane is not measured but computed. The steps 1 through 6 are repeated for all illumination rays with the different tilt angles chosen.

Incidentally, the illumination ray angle is defined as the angle of the ray relative to the sample surface. Therefore, different illumination ray angles can be achieved by rotating either the tilted illumination ray or the sample around the optical axis of the imaging system. However, rotating the sample is expected to be easier than rotating illumination ray, if the sample is not bulky. Therefore, sample rotation may be preferred in a majority of cases even if it requires an additional coordinate transformation of the image plane if the image sensor is not rotated accordingly.

When all the data collection and preprocessing steps are finished, the pupil synthesis can be started. Pupil synthesis is carried out by orienting correctly and combining coherently all the complex amplitude data at the pupil plane. The coherent combination of all the complex amplitude data at the pupil plane is facilitated by the multiple complex amplitude data extending over the overlapping regions in the pupil plane as described previously. The pupil synthesis step produces the complex amplitude distribution over the synthetically extended pupil area. Finally, the complex amplitude distribution over the synthetically extended pupil area is inverse-Fourier-transformed to get the super-resolution complex amplitude of the image-forming field. Note that, as usual, the sequence of processing steps shown in FIG. 13 does not need to be followed strictly but can be changed in many different ways as long as the next step does not need the result from the previous step.

Figure 14A:
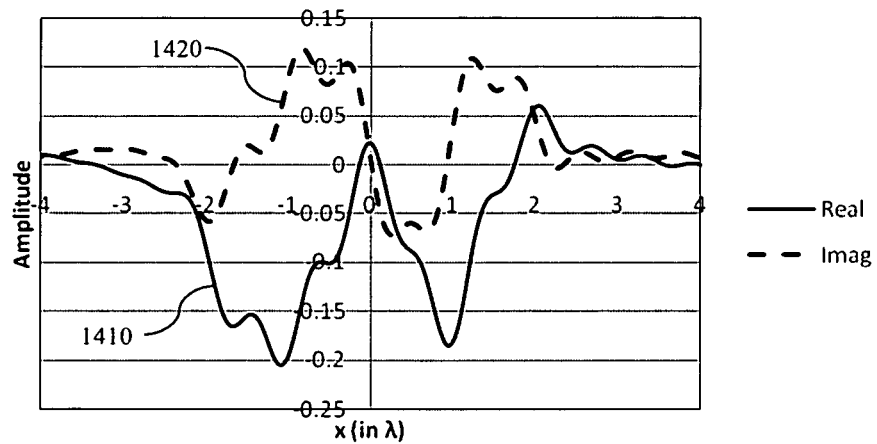
FIG. 14A shows the complex amplitude of an interferometric image of the one dimensional object shown in FIG. 7A with a +0.7 NA tilted illumination ray.

FIGS. 14A through 16B show an example of a super-resolution mode of operation. FIG. 14A shows the complex amplitude of an interferometric image of the same one-dimensional object shown in FIG. 7A with a tilted illumination ray. The real part is plotted as solid-line curve 1410 and the imaginary part is plotted as dashed-line curve 1420. The sine or numerical aperture of the tilt angle of the illumination ray is +0.7. This also equivalent to the direction cosine. The complex amplitude of the interferometric image is computed using the method presented in the Theory section and is shown in FIG. 14A. It is significantly different from that shown in FIG. 8 because of the different illumination ray angle. The Fourier-transform of the complex amplitude shown in FIG. 14A is shown in FIG. 14B, with the real part is plotted as solid-line curve 1430 and the imaginary part is plotted as dashed-line curve 1440. . The comparison of FIG. 14B with FIG. 10C shows that the tilt of the illumination ray determines the shift of the collection window of the spatial frequency contents of the object.

Figure 14B:
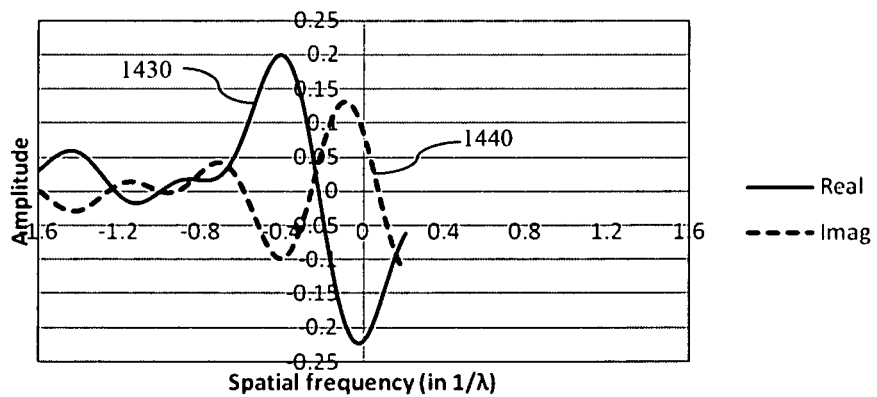
FIG. 14B shows the Fourier-transform of the complex amplitude shown in FIG. 14A.
Figure 15A:
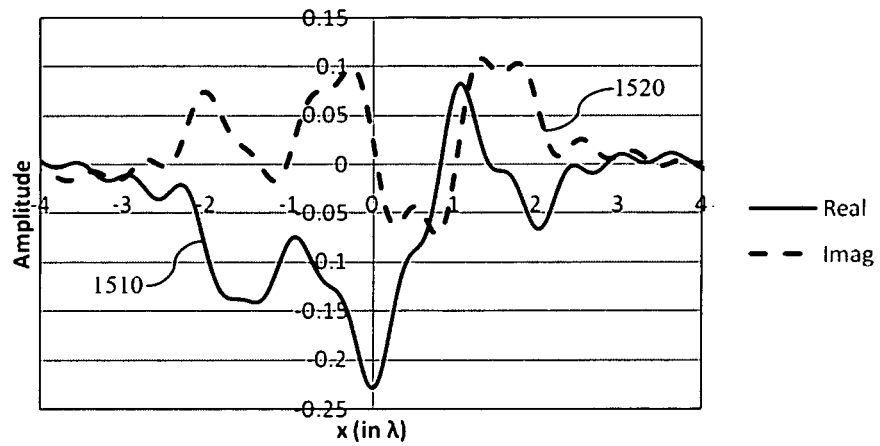
FIG. 15A shows the complex amplitude of the interferometric image of the one dimensional object shown in FIG. 7A with a −0.7 NA tilted illumination ray.
Figure 15B:
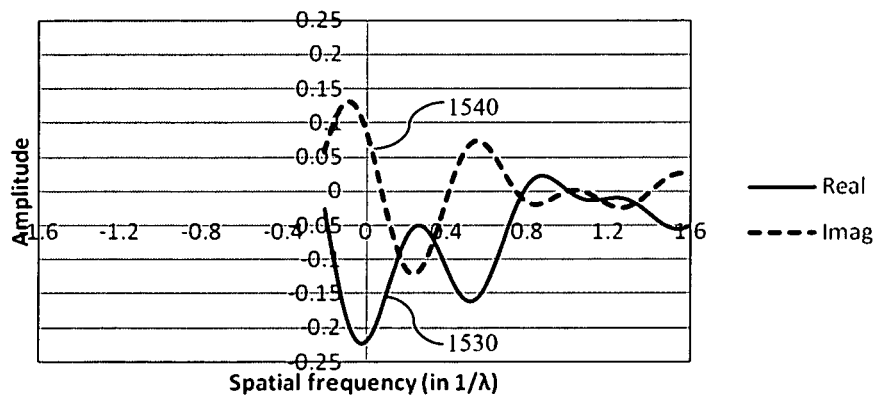
FIG. 15B shows the Fourier-transform of the complex amplitude shown in FIG. 15A.

FIG. 15A shows the complex amplitude of the interferometric image of the same one dimensional object shown in FIG. 7A with another tilted illumination ray. The real part is plotted as solid-line curve 1510 and the imaginary part is plotted as dashed-line curve 1520. This time, the sine of the tilt angle of the illumination ray is −0.7. That is, the illumination ray is tilted in the opposite direction this time. The complex amplitude of the interferometric image obtained with the oppositely tilted illumination ray is shown in FIG. 15A. It is significantly different from that shown in FIGS. 8 and 14A because of the different illumination ray angle. The Fourier-transform of the complex amplitude shown in FIG. 15A is shown in FIG. 15B, wherein the real part is plotted as solid-line curve 1530 and the imaginary part is plotted as dashed-line curve 1540). The comparison of FIG. 15B with FIG. 10C and 14B shows that the tilt of the illumination ray in the opposite direction is equivalent to a shift of the collection window of the spatial frequency contents of the object in the opposite direction. Thus, a tilt of the illumination ray allows us to collect higher spatial frequency contents of the object than those that are collected with a normally incident illumination ray.

Figure 16A:
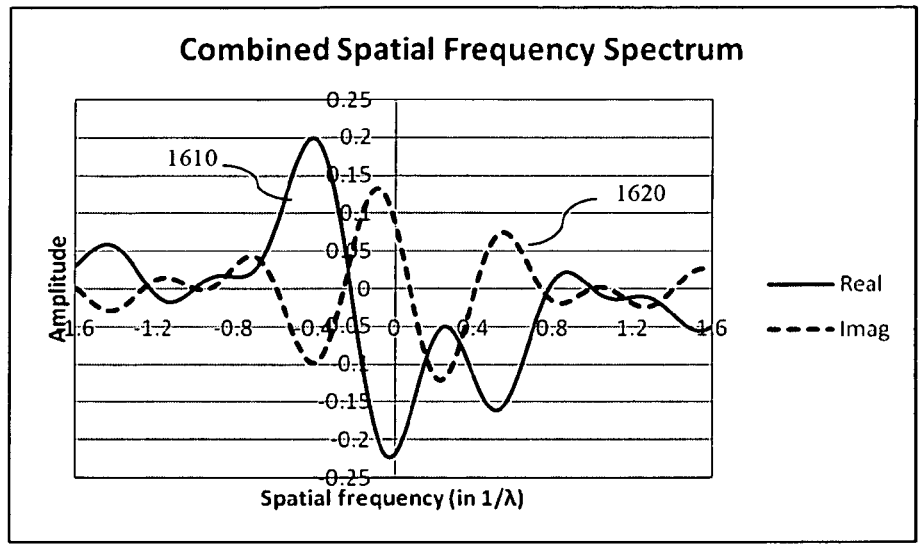
FIG. 16A shows the spatial frequency spectrum of coherently combined spatial frequency spectra shown in FIG. 14B and FIG. 15B.

The spatial frequency spectra shown in FIG. 14B and 15B have some amount of overlap. In this example, the overlapped region extends from −0.2 to +0.2 in terms of numerical aperture or direction cosine. Now, the spatial frequency spectra shown in FIG. 14B and 15B can be combined into one single spectrum coherently by best-matching the overlapped spectral region. The combined spatial frequency spectrum is shown in FIG. 16A, wherein the real part is plotted as solid-line curve 1610 and the imaginary part is plotted as dashed-line curve 1620. The combined spatial frequency spectrum extends from −1.6 to +1.6 in terms of numerical aperture or direction cosine. Note that the maximum theoretical NA achievable with a dry, coherently-illuminated, microscope objective without using the pupil synthesis technique disclosed herein is unity, whereas it approaches 2 for the super-resolution technique described herein. The maximum spatial frequency covered by the super-resolution technique is the same as that for conventional incoherent imaging systems but the image contrast differs substantially. The image contrast in a conventional system declines continuously from the lowest frequency to zero at the highest frequency, whereas in the super-resolution case the image contrast is maintained at unity up to the maximum limiting frequency. This leads to a much sharper image for the super-resolution case.

Figure 16B:
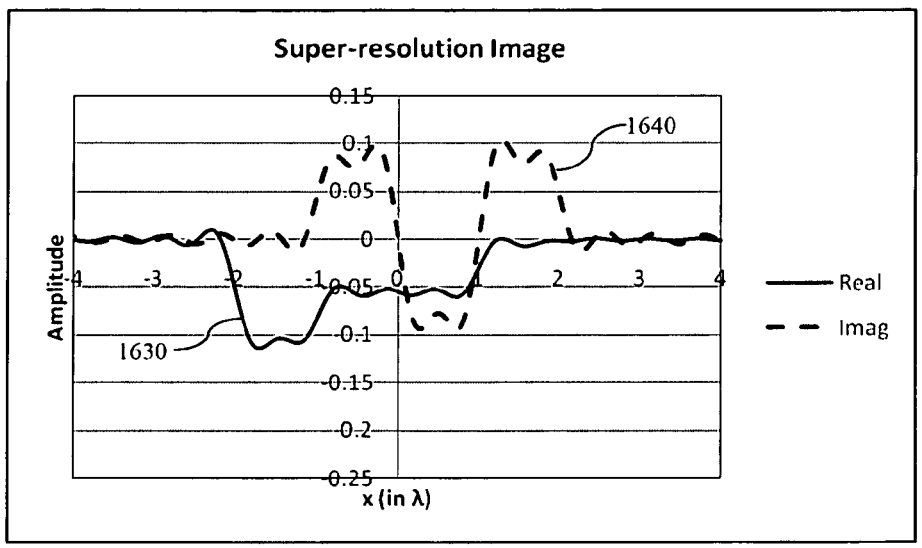
FIG. 16B shows the super-resolution image obtained by inverse Fourier-transforming the spatial frequency spectrum shown in FIG. 16A.

If the super-resolution case is compared with a coherently illuminated conventional system, the combined spatial frequency spectrum of the super-resolution system is much wider as shown in FIG. 10C. A wider spatial frequency spectrum leads to higher spatial resolution. This is shown in FIG. 16B, wherein the real part is plotted as solid-line curve 1630 and the imaginary part is plotted as dashed-line curve 1640. FIG. 16B is the final super-resolution image and was obtained by inverse-Fourier-transforming FIG. 16A. The comparison of FIG. 16B with FIG. 10A shows that the complex amplitude shown in FIG. 16B has much higher spatial resolution and depicts the object much more faithfully.

Figure 16C:
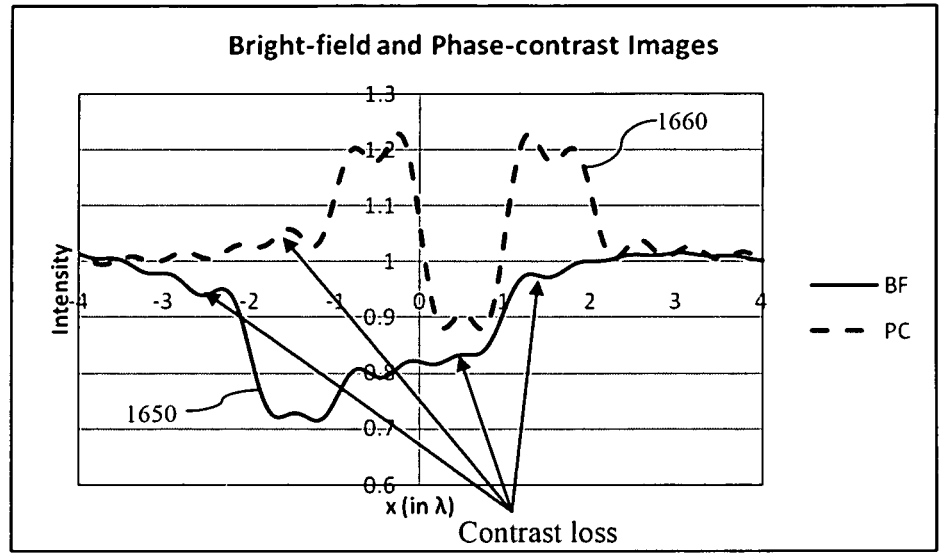
FIG. 16C shows the bright-field and phase-contrast images obtained with two symmetrically-tilted incoherent illumination rays.

FIG. 16C shows conventional bright-field and phase-contrast images of the same object obtained with the same two tilted illumination rays illuminating the sample incoherently. In FIG. 16C, the real part is plotted as solid-line curve 1650 and the imaginary part is plotted as dashed-line curve 1660. The comparison of FIG. 16C with FIG. 8 shows that, as expected, even the images taken in conventional ways with oblique illumination rays carry higher spatial frequency components than the images taken with normal illumination. However, the comparison of FIG. 16C with FIG. 16B shows that images taken in conventional ways are of lower contrast and less faithful to the original object than the images produced through the pupil synthesis technique disclosed herein. This kind of disparity in image quality is much greater in the images of two dimensional objects. Thus, the super-resolution or pupil synthesis technique disclosed herein cannot be emulated with conventional imaging techniques, thus interferometric imaging technology extends microscopy well beyond the realm of conventional imaging.

Figure 17:
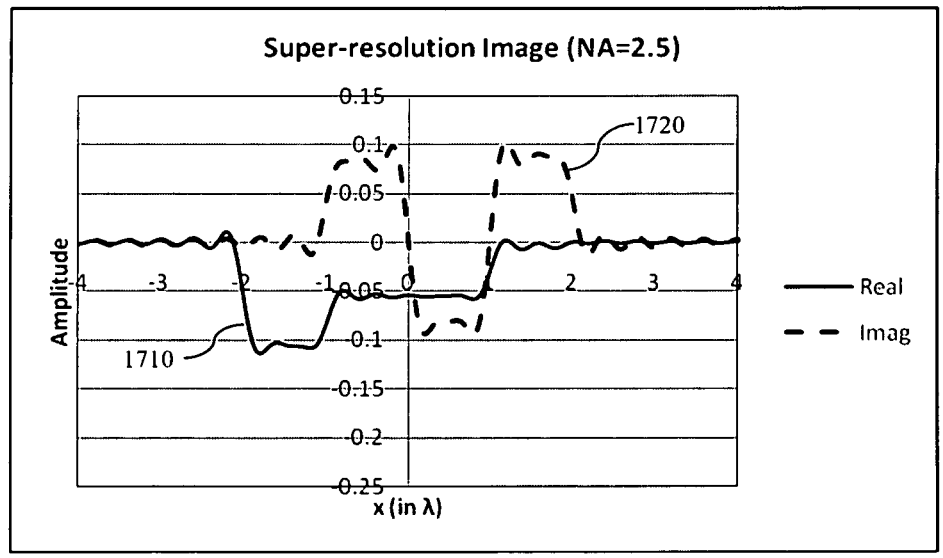
FIG. 17 shows another super-resolution image that can be obtained by using an immersion microscope and the pupil synthesis technique disclosed herein.

If an immersion microscope whose numerical aperture is larger than 1.0 is used for super-resolution imaging, even higher spatial resolution can be achieved. FIG. 17 shows an example, wherein the real part is plotted as solid-line curve 1710 and the imaginary part is plotted as dashed-line curve 1720. In this example, the numerical aperture is extended to 2.5 using the pupil synthesis technique disclosed herein. The image of the same object used in other examples shows much sharper edges than even the super-resolution image shown in FIG. 16B. Now, the image looks almost the same as the original object. The super-resolution technique disclosed herein allows us to obtain much sharper images than is possible with conventional imaging techniques.

The super-resolution technique can be combined with the tomographic technique in order to get super-resolution tomographic image of the sample. Tilting of the illumination ray has a similar effect to the tilting the sample. Therefore, in order to achieve finer volumetric resolution, more images with more illumination ray angles need to be collected and processed.

4. Phase-shifted Bright-field Mode.

This mode targets specific objects or types of samples. The relative phase between the scattered component and the unscattered component is usually set to maximize the image intensity of the specific objects or types of samples chosen. The signal-to-noise ratio of the image can be increased up to two times the intrinsic signal-to-noise ratio through noiseless amplification of the image-forming field by the unscattered component. Noiseless amplification is important for the imaging of faint objects. If the detailed physical characteristics of the object and surrounding patterns are unknown, the desirable or ideal relative phase value can be determined experimentally. For example, the complex-amplitude-mode can be run on the sample to determine the optimal phase value experimentally. On the other hand, if the physical characteristics of the objects are known, the optimum relative phase can be set based on theory or numerical simulations.

Equation (2) shows that $\phi_a$, the relative phase between the image-forming field and unscattered component, is an important variable for maximizing the image intensity. It shows that the image intensity is maximized when $\phi_a=0°$. This is because the interference term achieves a positive maximum when $\phi_a=0°$ and adds to the dark field term constructively. A weakly scattering phase object produces a $\phi_a=\pm90°$ so maximum contrast, in this case, is achieved with a phase shift of $\pm90°$.

As for the complex-amplitude mode, as long as the dynamic range of the image sensor is large enough, a strong unscattered component is generally preferred for a large noiseless amplification of the image-forming field. A strong unscattered component means a low contrast in the raw images. Thus, the way the new interferometric imaging system is operated is quite different than the way conventional microscopes or imaging systems are operated. Conventional microscopy tries to achieve the highest contrast in the raw images. However, the new disclosure tries to get highest image quality in the reconstructed images, not in the raw images.

5. Dark Field Mode.

The dark field mode is realized by completely blocking out the unscattered component. The dark field mode usually cannot produce a high quality image when the objects are small or weakly scattering due to the lack of any noiseless amplification of the weak image-forming field by the unscattered component, but is a good choice for imaging of relatively large or strongly scattering objects. The dark-field mode can provide amplitude information but cannot provide phase information. However, the dark-field mode can still be very useful because it can produce an image for any kind of object as long as the object scatters light relatively strongly. For example, it can form images of amplitude objects and phase objects at the same time. If one wants to know the viability of the dark field mode beforehand, the complex-amplitude mode may be run on the sample first and the strength of the dark-field term can be compared with the noise level.

Another good use of the dark field mode is finding the best focus for the image sensor. This is because the dark field mode blocks out the unscattered component, which does not carry any focus information, but still can affect the image critically during the focusing process through its interference with the scattered component. The dark field mode does not require as high a dynamic range on the image sensor, as other operational modes, because it does not have a unscattered component. Other important characteristics of the image sensor system for the dark field mode are high sensitivity and higher spatial resolution.

IV. Applications

The systems and methods disclosed herein are well-suited to various applications of optical imaging that benefit from the determination of both the amplitude and phase of the image-forming field and/or the super-high spatial resolution obtainable through the synthesis of an extended numerical aperture. The following is a partial list of potential applications:

- Bio-medical imaging
- High resolution measurement of surface topology
- Imaging of micro structures
- Imaging of alignment targets
- Overlay error measurement of circuit patterns
- Phase-contrast imaging
- High contrast imaging
- Complex amplitude measurement of reticle transmission or reflection
- Complex amplitude measurement of optical proximity correctors in OPC reticles
- Complex amplitude measurement of phase masks
- Optical inspection
- Defect review Displaying an Interferometric Image We are accustomed to seeing black and white pictures where the intensity of each pixel is conveyed by a gray scale value, and color pictures where the color and brightness of each pixel is proportional to that seen in the object. The addition of phase adds a whole new dimension to a picture, which is not easy to convey, and which might be conveyed quite differently depending on the application. If, for example, a chrome-on-glass photo mask is viewed, a consistent phase shift should be seen on the glass area and a different, but constant phase shift on the chrome area. However a scratch or a particle will generate a distinctly different phase value and it may be advantageous to bring this difference to the viewer's attention perhaps by circling the anomalous area or flashing the discrepant pixels. If a single color is used in the illumination system then nothing is lost if color is used to convey the phase shift between the scattered and unscattered beams with, for example, deep blue representing a zero degree phase shift and deep red representing a 359 degree phase shift. This scheme would work well when examining a pillar and hole pattern etched into a glass plate since pillars and holes would be given different colors. Otherwise it might be difficult to distinguish between the pillars and holes.

Another possibility is a sample, such as a piece of granite, which has been polished very flat and which contains a wide variety of mineral compositions each of which introduces a different phase shift on reflection. The location and the proportion of each mineral can be determined by asking the computer to show only those pixels that exhibit a phase-shift corresponding to the desired mineral. Comparing the pixels shown to the total number in the picture yields the proportion of that mineral in the sample. In situations where phase is not sufficient to distinguish a material from the other materials in the vicinity, then a combination of properties such as phase shift and amplitude, or phase-shift, amplitude and color could be invoked to identify a particular material. Each material could be represented by a false color in the display making identification very easy.

In the field of biology it is often difficult to distinguish one type of cell from another and often dyes are used to enhance the visible differences. Interferometric imaging opens the possibility of using phase and amplitude differences in transmission and reflection mode as well as color differences to distinguish one type of cell from another. If phase and amplitude prove to be insufficient in differentiating one type of cell from another then, the chemical differences between cells could be exploited by a technique similar to staining but employing a chemical which accentuates the phase and amplitude differences between like cells so they can be differentiated in an interferometric imaging system.

If an arrangement is used to measure both the transmissive and reflective properties of the sample yielding an amplitude and a phase value in either case, then the ability of the interferometric imaging system to differentiate between different materials is further enhanced. For example the absorption of energy in a feature can be estimated if both the reflected and transmitted amplitudes or intensities are known, and differences in absorption can often be used to distinguish one material from another. Thus a useful display mode might be one that shows the variation in absorption across the sample either by a brightness variation or by changing the display color as a function of sample absorption.

Operator Interface

Having access to a sample picture that includes both amplitude and phase data for each pixel opens a world of possibilities on how the data can be used and displayed. Distinguishing one type of material from another or one type of cell from another can lead to new applications or valuable extensions to existing applications such as counting and classifying various types of blood cells. A general-purpose interferometric imaging system would need a very flexible operator interface so that a phase and amplitude picture stored in the computer could be manipulated and displayed in a wide variety of ways including those described above.

Image Sensing System

The image sensing system includes a detector array located in the image plane that senses the intensity of the scattered and substantially unscattered components after they have interfered with each other. The resultant intensity, which is the square of the linear superposition of the unscattered and scattered components, depends on the phase relationship between the unscattered and scattered components. As is shown in the Theory section, it turns out that by changing the phase between the scattered and unscattered components by known (select) amounts, and by making a minimum of three measurements, each with a different phase shift, it is possible to calculate the phase and amplitude of the scattered radiation reflected or transmitted from a pixel location on the sample. The detector output is converted to a stream of numbers proportional to the intensity incident on each detector in the array, which is stored as a raw picture (raw image). In this case, each pixel is represented by a single number proportional to the intensity. The size of each pixel on the detector is preferably less than $\lambda/2NA$ to avoid aliasing in the image, where the NA in this case refers to the NA at the detector plane.

Image Processing System

The image processing system may be described as a system for converting a set or group of "raw" pictures received from the image sensor into a processed picture and then optionally into an "enhanced" picture. It may be desirable to keep a copy of each picture as it progresses from one step to another. The starting point is a so-called raw picture obtained directly from the image sensor, the output of which is converted into a stream of numbers by an A/D convertor. Each number represents an intensity measured at a specific pixel location on the sample surface and each array of numbers represents a picture corresponding to a specific phase shift between the scattered and unscattered components. A raw picture can be displayed as a 'black and white picture" where the brightness of each pixel is proportional to the intensity value. Typically 3 or more raw pictures, each corresponding to a different phase shift, are required to make up a raw picture set that can be processed to yield a single processed picture. Each pixel in a processed picture has an amplitude and a phase, i.e. two independent numbers that might be represented by a brightness and a color. The conversion of a raw data set into a processed picture could be accomplished in a first computer module or signal processing system which stores multiple raw pictures of the sample corresponding to different phase shifts and from these raw pictures computes a new, processed, picture of the sample. Sometimes the processed picture can be viewed directly to obtain the desired information. In this case the brightness of a pixel can be proportional to its amplitude, or more usually, its amplitude squared, and the phase represented by a color.

Sometimes it is necessary to employ the power of the computer to examine the whole data set representing the processed picture and artificially enhance those pixels meeting a specific criterion such as a certain range of amplitude and phase. This can be done with a second computer module or signal processing system that accepts the processed picture from the first computer module, and using preselected criteria, converts each pixel into a color and brightness level so that it can be displayed as a picture on a flat panel or similar display device or stored. In some cases pixels containing certain combinations of phase shift, and amplitude may be given enhanced brightness, or they may be tagged so that when displayed they exhibit a rapidly varying brightness and/or a special color to improve their contrast with respect to the other picture elements. The output from the second computer module is an enhanced picture or data set, in which the brightness and color of the pixels are determined by the corresponding value in the processed picture and by the preselected criteria. In this case some features are rendered more noticeable and others less noticeable.

Interferometric Imaging Control System

The previous discussion has shown how an interferometric imaging system can be employed to derive the phase and amplitude of each pixel of a sample image and how the resolution of the sample image can be substantially increased by combining a series of images, each of which is illuminated at a different off-axis azimuth angle. The phase and amplitude information of each pixel is particularly useful for measuring topographies, finding and identifying contaminants on a mask or wafer and for identifying different materials in an image. Increasing the resolution limit is useful when studying small objects that are approaching the resolution limits of a conventional microscope. There will undoubtedly be cases where one or the other or both techniques are required. Thus a very flexible control system is needed, which can accept a wide variety of operating modes from the operator and assist the operator in finding the best way of displaying the resultant image. In some cases it may be desirable to perform an analysis of the field of view such as counting the number of cells meeting a certain phase and amplitude criteria or measuring the fraction of the field of view occupied by a material characterized by a certain range of phase and amplitude. In order to get better statistics it may be desirable to study an area larger than that permitted by the microscope field of view. Thus it is also desirable that the control system be made capable of automating tasks such as counting and measuring and that it have control over an automated object stage so that multiple images can be obtained from samples larger than the microscope field of view.

In some applications, such as defect review after an IC mask or IC wafer inspection, it may be desirable to locate a single pixel in the image that describes the defect. In this case it is necessary to equip the stage with an accurate metrology system so that the stage can be moved accurately from a reference mark or marks on the substrate to the defect location. Generally it is necessary to compliment the stage metrology system with an accurate measurement of the magnification between the substrate and the detector array so the position of off-axis pixels in the detector can accurately estimated.

In some cases a pattern recognition capability may prove to be desirable so that objects with a distinctive shape can be identified, located and perhaps counted. Pattern recognition may also prove to be useful in identifying overlapping objects or objects butted together in a field. Therefore a control system for an interferometric imaging system should desirably accept a wide variety of operator inputs for sequencing the operation of the interferometric imaging system and for controlling the flow of data from the image sensing system through the data processing system to the display system.

In an example embodiment, the control system is linked to at least one of the following subsystems:
The operator interface
The phase shifter
The polarization control system
The focus sensing system and the focus adjusting system
The light source
The X & Y (lateral) position coordinates of the sample stage and controls to change the stage position
The angular position of the illumination system with respect to the sample
The image sensor
The raw picture archive and the processing module that processes the raw pictures to obtain a processed picture that contains phase and amplitude information
The aperture synthesis module that synthesizes a spatial frequency spectrum corresponding to each processed picture of the sample, links together adjacent frequency spectra of the same sample, and inverse-Fourier-transforms the linked spectra to produce a high-resolution processed picture. This module contains a spatial frequency spectrum archive that is accessible to the control system.
The processed picture archive and the processing module that converts a processed picture into an enhanced picture and the enhanced picture archive.
The display system module that converts an enhanced picture into a signal stream compatible with the display, including a display linked to the web.
The display
The pattern recognition system
The system test and calibration system
The system that processes processed pictures to identify and count features with certain properties and/or to measure the fractional area occupied by features meeting certain criteria.
The system that automates the processing of additional fields
The web in order to receive information, such as software and instruction manual upgrades and instructions for converting processed pictures into enhanced pictures, and to disseminate information such as sample pictures and system test and calibration results.

Control System Operational Sequence

An example embodiment of a sequence of operations executed by a control system in carrying out the method of the disclosure is as follows: The operator indicates that an enhanced resolution picture of the sample is required using the superposition of six illumination angles and that each processed picture used in the aperture synthesis be derived from 3 raw pictures differing in phase by 120°. The p-polarization direction is to be used both for the incident illumination and for the detected illumination. The data is to be deconvolved to correct for the finite size of each detector element and in the final enhanced picture any pixel with a normalized amplitude between 0.2 and 0.3 and with a phase between 180° and 200° shall be colored black. After positioning the sample on the object stage the operator hits the "go" button.

1. The sequencer activates the focus system and waits till good focus is achieved.
2. The phase shifter is set at −120° and the polarization optics is oriented so that the beam incident on the sample is p-polarized and the light received by the detector is also p-polarized.
3. The first angular position of the illumination system with respect to the sample is set.
4. The light source is activated and the detector array takes a picture of the sample
5. The detector signal is digitized and passed to the raw picture module which deconvolves the finite detector width and then properly archives it and places it in the operational memory
6. The phase shifter is incremented 120°.
7. Steps 4 through 6 are repeated twice to obtain 3 pictures
8. The 3 raw pictures in the raw picture module are processed to produce a single processed picture, which is then passed to the aperture synthesis module where it is archived and placed in operational memory.
9. The second angular position of the illumination system with respect to the sample is set and steps 4 through 8 are repeated
10. Step 9 is repeated through all 6-illumination angles resulting in six pictures in the operational memory of the aperture synthesizer.
11. Each of the six pictures is given the same sample orientation and then is Fourier-transformed to produce 6 overlapping frequency spectra.
12. The spatial frequency coordinates of the overlapping spectra are adjusted to yield good agreement, and the overlapping data points are averaged together to produce a single, large frequency spectrum.
13. The large frequency spectrum is inversely transformed to produce a high-resolution image, which is transferred to the display module.
14. The display module generates an enhanced picture by converting every amplitude to a brightness and every phase angle to a color except for any pixel with a normalized amplitude between 0.2 and 0.3 and with a phase between 180° and 200° which are colored black. The enhanced picture is archived and sent to the display module.
15. The display system module converts the enhanced picture into a signal stream compatible with the display, taking care to match the resolution of the picture to the resolution of the display
16. The enhanced picture is displayed The above sequence is only one of many possible sequences. Instead of taking 3 raw pictures and using an exact solution to obtain a processes picture, six raw pictures could be taken and a least squares regression analysis used to obtain each processed picture. This would take longer but would improve the signal to noise ratio. If there were known aberrations in the optical system their effects could have been removed from the processed picture as well. Similarly aperture synthesis from 6 illumination angles is only one of many possibilities ranging from 1 to a dozen illumination angles. There is an unlimited variety of ways to transform a processed picture into an enhanced picture and there was no attempt in this example to gather statistical results from the image or to automate the procedure so that a large area of the sample could be examined. Developing the best algorithm to transform a processed picture into an enhanced picture for a particular application probably requires a trial and error approach where the operator can iterate between the processed and the enhanced image while modifying the instructions to create the enhanced image. This might require a "test" mode of operation, which provides the operator with a moveable display cursor that generates phase and amplitude information for the pixel on which it is registered.

Many of the advantages of the various embodiments have been described herein. Such advantages include: extraction of both amplitude and phase information; high image contrast; the capability for super-high spatial resolution; the capability for aberration correction; avoidance of the need for speckle busting leading to lower cost; ability to use full-field illumination thereby decreasing the chance of sample damage; ability to use coherent illumination leading to well-defined diffraction orders, thereby providing for straightforward Fourier filtering; simple system configuration leading to lower cost; and efficient energy use.

Although the foregoing has been described in some detail for purposes of clarity, it will be apparent that certain changes and modifications may be made without departing from the principles thereof. It should be noted that there are many alternative ways of implementing both the processes and apparatuses described herein. Accordingly, the present embodiments are to be considered as illustrative and not restrictive, and the inventive body of work is not to be limited to the details given herein, which may be modified within the scope and equivalents of the appended claims.

What is claimed is:

1. A common path, interferometric imaging system for forming a resolution-enhanced image of a sample, comprising:
    an illumination source that sequentially illuminates the sample from different directions to form for each illumination a plurality of substantially unscattered light components and substantially scattered light components that have a relative phase;
    an optical imaging system that has a pupil and that, collects and images the substantially scattered light components and the substantially unscattered light components for each illumination, wherein the substantially scattered light components, and the substantially unscattered light components pass through a portion of the pupil;
    a variable phase shifting system located substantially at the pupil and that varies said relative phase by at least three different amounts for each illumination;
    a detector having an array of pixels that sense for each illumination an intensity of combined portions of the substantially scattered light component and the substantially unscattered light component after the relative phase is adjusted and after they have interfered with one another, and that generates in response thereto at least three raw images; and
    processing means operably connected to the detector for receiving and processing the at least three raw images for each illumination and forming therefrom a complex amplitude of an optical field for each detector pixel, and Fourier-processing the complex amplitudes for each illumination to form the resolution-enhanced image of the sample.

2. A system according to claim 1, wherein the processing means:
Fourier-transforms the complex amplitudes to obtain a plurality of spatial frequency spectra;
orients the plurality of spatial frequency spectra;
coherently merges the oriented spatial frequency spectra; and
inverse Fourier-transforms the coherently merged and oriented frequency spectra.

3. A system according to claim 1, further comprising a sample positioning system configured to support and position the sample substantially in an object plane of the optical imaging system with respect to a coordinate system.

4. A system according to claim 1, further comprising at least one pupil filter located substantially at the pupil and configured to substantially block light from the sample associated with at least one sample feature.

5. A system according to claim 1, wherein the variable phase shifting system includes a phase shifting plate containing multiple phase-shifting elements each having a known phase shift.

6. A system according to claim 1, wherein the variable phase shifting system adjusts a phase of the substantially unscattered light components.

7. A system according to claim 1, further including:
a polarization control system configured to control a polarization of light from the illumination source and a polarization of the light reaching the detector.

8. A system according to claim 1, wherein the optical imaging system includes a transmission optical system and a reflection optical system.

9. The system of claim 1, further comprising a display system adapted to display at least one of: one or more raw sample images, one or more complex amplitude images, one or more spatial frequency spectra, and one or more resolution-enhanced images.

10. A common-path interferometric method of forming a resolution-enhanced image of a sample, comprising:
sequentially performing a plurality of illuminations of the sample at different directions relative to the sample to form a plurality of substantially unscattered light components and a substantially scattered light components;
collecting the substantially scattered light components and the substantially unscattered light components with an optical imaging system having a pupil, wherein the substantially scattered light components and the substantially unscattered light components have a relative phase, and wherein the unscattered components pass through a portion of the pupil;
for each illumination, adjusting substantially at the pupil said relative phase by two or more amounts;
sensing combined portions of the substantially scattered light components and the substantially unscattered light components after said relative phase adjusting to generate a set of raw sample images for each illumination;
processing each set of raw sample images to define a complex amplitude image for each illumination, and Fourier-transforming each complex amplitude image to define a corresponding spatial frequency spectrum for each illumination;
orienting and then coherently merging the spatial frequency spectra; and
inverse Fourier-transforming the coherently merged frequency spectra for the different illuminations to form the resolution-enhanced sample image.

11. A method according to claim 10, wherein the different illumination directions are achieved by rotating the sample relative to a fixed illumination direction.

12. A method according to claim 11, further comprising performing pattern recognition on the resolution-enhanced sample image.

13. A method according to claim 11, wherein said sensing is performed using an image sensor having an array of pixels, wherein each pixel measures an intensity, and further including normalizing the detector pixel intensity.

14. A method according to claim 10, wherein the relative phase is adjusted for each illumination by three different amounts.

15. A method according to claim 10, further comprising defining a polarization state for the illumination.

16. A method according to claim 10, further comprising attenuating the substantially unscattered light components.

17. A method according to claim 10, wherein adjusting said relative phase includes using at least one of a phase-shifting plate, a phase-shifting mirror and an electro-optical phase shifter.

18. A method according to claim 10, wherein said sensing is performed using a sensor array having detector elements with a finite size and performing a deconvolution on the raw sample images to substantially compensate for said finite size detector elements.

19. A method according to claim 10, further comprising removing at least one of distortion and optical aberrations from each complex amplitude image.

20. A method according to claim 10, further comprising optimizing a contrast of the processed sample images by varying a polarization of illumination and a polarization of the substantially scattered and substantially unscattered light components.

21. A method according to claim 10, including removing low-order spatial frequencies from the spatial frequency spectra.

22. A method according to claim 10, further comprising performing pupil filtering based on substantially attenuating or enhancing at least one feature of the sample.

23. A method of forming a resolution-enhanced image of a sample, comprising:
performing sequential illumination of the sample from different directions to form a corresponding plurality of substantially unscattered and a substantially scattered light components having a relative phase;
for each illumination, adjusting the relative phase to form phase-adjusted light components by at least three different amounts;
for each illumination, forming from the phase-adjusted components a set of raw sample images;
computing a complex amplitude image for each set of raw sample images;
Fourier processing the complex amplitude image for each set of raw sample images to form a set of spatial frequency spectra;
orienting and coherently merging the plurality of spatial frequency spectra; and
inverse Fourier-transforming the oriented and coherently merged frequency spectra to form the resolution-enhanced image of the sample.

* * * * *